US009126016B2

(12) United States Patent
Fulton

(10) Patent No.: US 9,126,016 B2
(45) Date of Patent: Sep. 8, 2015

(54) AUGMENTED DELIVERY CATHETER AND METHOD

(75) Inventor: Richard E. Fulton, Grand Junction, CO (US)

(73) Assignee: NFUSION VASCULAR SYSTEMS LLC, Grand Junction, CO (US)

( * ) Notice: Subject to any disclaimer, the term of this patent is extended or adjusted under 35 U.S.C. 154(b) by 0 days.

(21) Appl. No.: 13/111,924

(22) Filed: May 19, 2011

(65) Prior Publication Data

US 2011/0288529 A1  Nov. 24, 2011

Related U.S. Application Data

(60) Provisional application No. 61/395,907, filed on May 19, 2010, provisional application No. 61/400,593, filed on Jul. 30, 2010.

(51) Int. Cl.
*A61M 25/04* (2006.01)
*A61M 25/00* (2006.01)

(52) U.S. Cl.
CPC .......... *A61M 25/04* (2013.01); *A61M 25/0084* (2013.01)

(58) Field of Classification Search
CPC ............ A61M 25/0084; A61M 25/04; A61M 2025/0057; A61M 2025/1052; A61M 2025/1081; A61M 25/10; A61M 25/1011; A61M 25/104; A61M 2025/105; A61M 25/005; A61M 25/0074; A61M 25/0075; A61M 29/02; A61M 2025/0004; A61M 2025/0006; A61M 2025/0073; A61M 2025/09183; A61M 2025/109; A61M 25/00; A61M 25/0041; A61M 25/0045; A61M 25/0053; A61M 25/0068; A61M 25/007; A61M 25/0071; A61M 25/0082; A61M 25/0119; A61M 25/0662; A61M 25/09; A61M 25/1006; C12N 15/113; C12N 15/1136; C12N 2310/14; A61L 29/16; A61L 2300/416; A61L 2300/258; A61F 2002/018; A61F 2230/0006; A61F 2230/0067; A61F 2250/0067; A61F 2/013; A61F 2/90; A61F 2/958; A61F 2230/008; A61F 2/01; A61F 2002/072; A61F 2230/0008; A61F 2230/0069; A61N 1/327; A61B 17/221; A61B 17/00491; A61B 17/12186; A61B 17/22; A61B 17/22031; A61B 17/32056; A61B 17/22034; A61B 2017/22082; A61B 2017/2212; A61B 2017/2215; D04B 1/16; D04C 1/02; D04C 3/48
USPC ................. 604/508, 510, 175, 104, 107, 108; 606/200
See application file for complete search history.

(56) References Cited

U.S. PATENT DOCUMENTS

| | | |
|---|---|---|
| 5,078,685 A | 1/1992 | Colliver |
| 5,632,754 A | 5/1997 | Farley et al. |
| 5,910,150 A | 6/1999 | Saadat |
| 5,916,235 A | 6/1999 | Guglielmi |
| 5,947,995 A | 9/1999 | Samuels |
| 6,238,412 B1 | 5/2001 | Dubrul et al. |
| 6,635,068 B1 | 10/2003 | Dubrul et al. |

(Continued)

*Primary Examiner* — Kami A Bosworth
*Assistant Examiner* — Imani Hayman
(74) *Attorney, Agent, or Firm* — Wilson Sonsini Goodrich & Rosati

(57) ABSTRACT

The present invention relates to a catheter apparatus with an anchoring device to stabilize the catheter tip when in use, such as when infusing, injecting, or delivering substances, devices or other catheters into a patient. The apparatus according to various embodiments deploys an anchoring device that stabilizes the catheter tip and enables adjustment of the blood flow during use.

52 Claims, 12 Drawing Sheets

(56) References Cited

U.S. PATENT DOCUMENTS

| | | |
|---|---|---|
| 6,695,858 B1 | 2/2004 | Dubrul et al. |
| 6,699,260 B2 | 3/2004 | Dubrul et al. |
| 7,232,453 B2 * | 6/2007 | Shimon .................. 606/200 |
| 7,241,257 B1 | 7/2007 | Ainsworth et al. |
| 7,645,296 B2 | 1/2010 | Theron et al. |
| 2002/0161394 A1 * | 10/2002 | Macoviak et al. ............ 606/200 |
| 2004/0260333 A1 | 12/2004 | Dubrul et al. |
| 2005/0187570 A1 * | 8/2005 | Nguyen et al. ................ 606/159 |
| 2010/0030256 A1 | 2/2010 | Dubrul et al. |
| 2010/0114113 A1 | 5/2010 | Dubrul et al. |
| 2012/0116351 A1 * | 5/2012 | Chomas et al. ............... 604/508 |

* cited by examiner

AUGMENTED DELIVERY CATHETER AND METHOD

CROSS REFERENCE TO RELATED APPLICATIONS

This application claims the benefit of U.S. Provisional Patent Application No. 61/395,907, entitled "AUGMENTED DELIVERY CATHETER AND METHOD", filed on May 19, 2010, and U.S. Provisional Patent Application No. 61/400,593, entitled "DEVICES AND METHODS OF TREATING VENOUS DISEASE", filed on Jul. 30, 2010, the entire disclosure of each of which is incorporated by reference herein.

FIELD OF THE INVENTION

This disclosure relates to a catheter with an anchoring device to stabilize the catheter tip when in use, such as when infusing, injecting, or delivering substances, devices or other catheters into a patient.

BACKGROUND OF THE INVENTION

Catheter technology is widely utilized to diagnose many abnormalities, to treat vascular disease, to perform vascular interventions, to deliver devices to occlude vessels, and to focally deliver agents to tissues, among other uses. The catheter technology employed will vary depending on the surgical procedure and the nature and extent of the injury. For a general background on catheter technology and some of the tools and apparatus used involving catheters, see U.S. Pat. No. 5,910,150 issued to Saadat on Jun. 8, 1999 ("Saadat"), the entire disclosure of which is incorporated herein by reference in its entirety. In addition, further background on catheter technology and some of the tools and apparatus used involving catheters is found in U.S. Pat. No. 7,241,257 issued to Ainsworth et al. on Jul. 10, 2007 ("Ainsworth"), the entire disclosure of which is incorporated herein by reference in its entirety.

Some attempts have been made to develop catheters useful and adaptable for multiple applications, see U.S. Pat. No. 5,632,754 issued to Farley et al. on May 27, 1997 ("Farley"), the entire disclosure of which is incorporated herein by reference in its entirety.

Many times the stability of the catheter tip is not problematic or critical to the procedure, but routinely the stability of the catheter tip is indeed important to the success of the particular procedure. In many cases a "guide" catheter is inserted and the tip is placed within or near the orifice of the vessel intended to be treated. See for example U.S. Pat. No. 5,947,995 issued to Samuels on Sep. 7, 1999 ("Samuels"), the entire disclosure of which is incorporated herein by reference in its entirety.

The interventional device catheter of choice, whether it is an angioplasty balloon catheter, a stent delivery device, an atherectomy device, or some other specialized catheters, is then placed coaxially through the guide catheter to effect the desired intervention. In the case of coronary angioplasty, stent placement, or other intervention, the guide catheter frequently "backs out" of the coronary orifice when a guide wire or the interventional device catheter is advanced through the narrowed lesion, or attempts are made to advance through the narrowed lesion, because of the resistance caused by the lesion. For a general background on stenting and guiding catheters, see U.S. Pat. No. 7,645,296 issued to Theron et al. on Jan. 12, 2010 ("Theron"), the entire disclosure of which is incorporated herein by reference in its entirety.

This results in repeated attempts to cross the lesion, change the catheter/guide wires, predilation with a smaller catheter, reinsertion of the original catheter, and so forth, and adds additional risk and cost to the procedure. In the case of chronic total occlusions (CTO's), the crossing of the CTO can be extremely difficult as there is a complete occlusion without a lumen that provides resistance to the passage of the guide wire and interventional device. Moreover, since there is no lumen in CTO's, there is a need to center the lumen of the catheter within the lumen of the vessel to lessen the chance of subintimal dissections by the guide wire. In other words, an eccentrically positioned guide wire has a greater chance of tracking subintimally along the outer circumference of a vascular lumen than does a guide wire positioned centrally within the lumen.

Similarly, in the endovascular treatment of carotid artery lesions, the acute angles, especially at the origin of the left common carotid artery, create difficulty in advancing the stent delivery catheters as the guide catheters tend to back out of the orifice when the stent delivery catheters are advanced.

This results in repeated attempts at positioning the catheters, changing the catheters, and added risk and cost to the procedure. The risk of stroke increases with the difficulty of the procedure.

In fact, the same type of problem occurs with regularity anywhere in the body in which a catheter or guide wire is attempted to be pushed through a tight stenosis. The resistance of the stenotic lesion, along with the curvature of the arteries, prevent enough forward force or "pushability" to advance the interventional devices through the lesion easily. Most vascular catheterizations are done with a percutaneous approach through the femoral artery or vein. As will be shown, in the arterial system, the catheters must then take a circuitous route through the aortic arch to access most any vessel supplying the head and neck, upper extremity, and the heart. The vessels in the abdomen branch in an acute angle (with respect to the femoral approach) making them difficult to access also. While the vessels of the lower extremity may be approached with an antegrade puncture in the ipsilateral femoral artery, accessing and treating them may present similar problems as above if the access is done from the contralateral femoral artery. In sum, there is very infrequently a vessel that is subjected to an endovascular intervention of any type in which there is a more or less straight line of force to place and advance the catheter tip from the femoral access point. The resulting forces are frequently not in the direction of the catheter tip, causing the catheter tip's purchase within the selected vessel to be tenuous, especially since the heart is contracting and the aorta is pulsating. The combination of the tortuous path the catheters must take, the resistance within the vessel caused by vessel tortuosity or the constricted lesion, and the pulsations of the heart and the aorta combine to make vascular interventions more difficult, more costly, and more risky to the patient than is generally perceived.

Different catheter shapes and configurations have been developed to access problematic arteries, but frequently the choice of a specialized shape is made only after repeated attempts to catheterize an artery or to perform an intervention within an artery have failed. Sometimes a shape is chosen which is successful in catheterizing an artery, but the interventional device cannot be passed through the catheter or guide catheter to the lesion without dislodging the guide catheter. Pushing the inner catheter against tortuous vessels or a tight stenotic lesion essentially pushes the guide catheter out of the orifice of the vessel. The difficulties described above in the current procedures and devices are overcome, as discussed, by changing out the catheters, using other methods and devices, albeit at increased cost and risk, to achieve the desired result.

In other interventions, substances or devices are injected or delivered into certain arteries in which it is critical that the catheter tip is stable and there is no movement at all, less the patient may suffer serious and even fatal sequelae. One of these vascular interventions involves infusing concentrated chemotherapeutic agents directly into an artery supplying an organ to treat tumors within that organ. The following description involves placing a catheter in the hepatic artery and serves as an example of the problems associating with delivering a substance or device into arteries.

There are several methods of treating cancerous tumors including surgery, chemotherapy, focal ablation by delivery of various forms of energy, radiation, among others. Often, tumors are not resectable by surgery because they have spread into the surrounding tissue or to distant tissue, such as the liver, lung, or brain. The treatment of metastatic disease to these organs is done with chemotherapy, focal surgical resection, focal ablation and occasionally radiation when there are only a few lesions. Oftentimes, the metastatic disease is diffused and not amenable to surgery, radiation or focal ablation. This leaves chemotherapy as the only alternative, and the effectiveness of the intravenous chemotherapy is limited by the systemic toxicities caused by the drug, including bone marrow suppression, neutropenia, nausea, diarrhea, anorexia, wasting, cachexia, bacterial or viral overgrowth among others.

Often perfusion of the organ containing the tumor or tumors with a chemotherapeutic agent is performed. This may be done by simply injecting the chemotherapeutic agent directly into the artery supplying the organ, or by chemoembolization in which the chemotherapeutic agent is mixed with or attached to some substance before it is injected. The injection may be made into a branch artery that supplies the targeted tumor rather than in the main artery to the organ. This has been referred to as selective chemoembolization. Substances mixed with or attached to the chemotherapeutic agent include gelfoam, lipiodal, and other substances. The chemotherapeutic agent may be coated on small beads that are embolized to the tumor as drug eluting beads (DEB's.) The beads that are embolized may instead carry a radioactive substance, such as Yttrium 90, a beta emitter. Collectively, methods and substances that combine radiation or chemotherapeutic agents with a carrier are termed "embolics." The selective injection into the branch artery supplying the tumor insures the embolization of the beads, containing either chemotherapeutic agent or a radioactive agent, to the tumor bed where the beads lodge in small arterioles and the substance attached to the beads acts upon the tumor over several days to weeks rather than the rather passive non-selective method of just injecting a chemotherapeutic agent into the artery which creates only a fleeting contact with the tumor. When the embolics are injected into an artery, they will eventually occlude the arterial branches and the artery, causing diminished to stagnant flow in the artery. In this case, there is a likelihood of reflux of the emoblics out of the intended artery causing them to embolize to other unintended arteries and organs. This may cause a litany of problems and complications, obviously. It is a purpose of the current invention to direct the chemotherapeutic agent or radioactive agent with or without embolics toward the target tumor or organ, to stabilize the catheter tip in appropriate position and to prevent reflux of the agents out of the intended vessel. Moreover, by controlling the flow through the current invention and the pressure distal to the tip of the device, the pressure distally can be kept lower than pressure proximally obviating any reflux.

A system, process, and method of isolated perfusion of organs with a very high dose of a chemotherapeutic agent, collection of the effluent venous blood from that organ before it enters the systemic circulation, filtering the chemotherapeutic agent from the collected blood, and returning the filtered blood without the chemotherapeutic agent to the systemic circulation has been described and has shown great effectiveness to date in treating tumors of the liver. In essence, a very high dose of a chemotherapeutic agent is infused into the hepatic artery over a period of time, usually from 30 minutes to an hour. The high dose chemotherapeutic agent perfuses the liver and is much more effective than a traditional systemic dose administered intravenously. This drug is taken up by the tumor and the remainder flows into the hepatic veins, which are a series of veins that drain from the liver into the upper inferior vena cava (IVC.) This blood which still contains toxic levels of the chemotherapeutic agent is collected by an isolation device which is part of this special apparatus. The hepatic infusion catheter which is placed percutaneously is usually a standard angiographic catheter. The hepatic venous blood isolation device is a double balloon system that is deployed in the inferior vena cava, the balloons being inflated above and below the hepatic veins, the hepatic venous effluent collected into a catheter and pumped through a filter outside the body that removes the chemotherapeutic agent, and returns to the superior vena cava via another catheter. A through lumen is provided to allow blood from the inferior vena cava to flow back to the heart while the balloons are occluding the vena cava.

While current devices are generally effective in treating the tumor or tumors of the liver, they are somewhat crude and cumbersome to use, as there sometimes is reflux of the toxic chemotherapeutic agent out of the hepatic artery and into arteries supplying the bowel, and the catheter tip may become dislodged from its place in the proper hepatic artery, retracting more proximally and infusing agent into arteries supplying the proximal small bowel, pancreas, spleen, and other organs. This is of great importance as the dose being infused may be up to ten times the usual intravenous dose, and hence can cause serious side effects if not collected as above before entering the systemic circulation. If it is not infused into the correct artery, it will not be collected by the venous recovery device, and this concentrated toxic substance will essentially be a local and systemic poison with which the body is unable to deal. Infusion catheters with a balloon on the distal end have been described, but the balloon must be expanded completely to produce stability of the distal catheter and, in doing so, obstructs the flow of the vessel and the flow of the infused material. While the current invention is described for infusion of a chemotherapeutic agent into the liver, it should be realized that the current invention could be utilized in other organs and regions of the body to infuse any number of medicines, substances, agents, particles, occlusive devices, stents, coils, and so forth in those different regions.

Furthermore, in perfusing the liver, the standard angiographic catheter which is placed in the hepatic artery usually is inserted via a femoral approach, traverses the iliac artery and abdominal aorta and then must be placed in the celiac axis which is frequently at a 135 degree or greater angle to the aorta, advanced further into the common hepatic artery, and finally placed with the tip in the proper hepatic artery which is a rather short artery. This tortuous path places some torque on the catheter, and patient motion, whether voluntary or from normal respiration or vascular pulsations, may cause the catheter tip to back out of the proper hepatic artery during the infusion of the chemotherapeutic agent. This causes the toxic chemotherapeutic agent to flow into vessels other than the intended ones, potentially damaging those tissues supplied by theses vessels, including the pancreas, duodenum, stomach, and spleen among others. Even if the catheter tip does not move and is stable, there is the possibility of reflux of the toxic agent out of the hepatic artery and into these adjacent arteries as spasm may develop in the hepatic arteries as a result of the infusion of the chemotherapeutic agent, or the infusion rate may exceed the flow in the hepatic artery for some other reason resulting in the volume being infused exceeding the capacity of the artery. The infused agent then refluxes out of the intended artery and into the surrounding vessels not intended for infusion causing the problems discussed above and even death. While the majority of cases of infusions may well be successful with the current prior art device, even a small minority of the infusion procedures that have complications would give the clinical oncologists and oncological surgeons who care for these patients concern and raise questions as to whether the procedure is truly safe. This doubt may prevent thousands, and potentially hundreds of thousands, of patients that may benefit from this therapy from receiving it and prolonging their lives.

Additionally, in the case of renal cell carcinoma, it is frequently advantageous to embolize coils or other materials into the renal artery before a nephrectomy. This creates a more or less bloodless field for the surgeon and makes the operation easier, safer, and quicker. It involves placing a catheter in the renal artery and delivering a special coil or other material to occlude the renal artery. The procedure is usually straightforward. In some cases, however, the catheter tip becomes dislodged, usually while attempting to place the second or third coil in the renal artery and the coil embolizes down the aorta and into a lower extremity or other vessel where it must be retrieved by catheters or by surgery. This is another example of catheter tip instability causing an iatrogenic complication.

In crossing a chronic total occlusion, sometimes there is a need to approach the lesion retrograde, or from a downstream location. Frequently the distal aspect of the CTO is easier to enter than the proximal arterial cap for several reasons. In this maneuver, the guide wire is passed from distally in a retrograde manner through the CTO and then the tip of the guide wire is captured by a snare inserted in a standard antegrade manner and then withdrawn through an antegrade catheter. This maneuver includes engaging the guide wire with the snare, then placing traction on the snare dragging the guide wire into the antegrade catheter and then out the external end of the antegrade catheter. When this is done, the guide wire is usually deformed and bent upon itself. This provides the operator with access that would otherwise not be possible. The current device placed antegrade upstream of the occlusion, with its funnel shape, could be utilized as a capture device to capture the guide wire placed in a retrograde manner through the occlusion. This may be important when the guide wire cannot be captured by a snare, bent on itself and easily fished out through the standard antegrade catheter. Additional uses of the current invention include capture of guide wires in any artery or vein, channel of the body, or tract or space, whether natural or surgically created.

Traditional catheter techniques or technologies to prevent or inhibit instability of a catheter as positioned within a patient can impart trauma to the patient and/or prevent or severely restrict blood flow.

For example, U.S. Pat. No. 5,078,685 issued to Colliver on Jan. 7, 1992 ("Colliver") provides a vascular catheter with an elongated, flexible tubular catheter body fitted with a rigid tunnel member. The tunnel member is intended to define an open, non-collapsible, longitudinal passageway for blood flow outside of the catheter body when the vascular catheter is inserted in a blood vessel of a patient. However, such a rigid collar-like member enables only imprecise degrees of pressure to be axially imparted to the blood vessel, thereby causing unnecessary trauma to the patient.

U.S. Pat. No. 6,238,412 issued to Dubrul et al. on May 29, 2001 ("Dubrul I"), and U.S. Pat. No. 6,695,858 issued to Dubrul et al. on Feb. 24, 2004 ("Dubrul II"), describe a catheter device for removal of a blockage in a passageway such as a dialysis graft or in a body passageway. The device of Dubrul I and II includes a traditional funnel-like catheter for reception and aspiration of the blockage and an occlusion engaging element supported on a wire that extends through the catheter. The device includes a braid device that expands against the blood vessel wall to stabilize the catheter and to prevent the occlusion from passing around the outside of the device; blood flow is also prevented from passing through the device.

U.S. Pat. No. 6,699,260 issued to Dubrul et al. on Mar. 2, 2004 ("Dubrul III") describes a catheter device for removal of a blockage in a body passageway fitted with a multi-wing malecot expansion device. Similar to Dubrul I and II, the Dubrul III device entirely blocks blood flow, and the targeted blockage, from passing around or through the device. Further, U.S. Pat. Pub. No. 2010/0114113 to Dubrul et al. published May 6, 2010 ("Dubrul IV") discloses a catheter device for occlusion removal that blocks blood flow.

U.S. Pat. Pub. No. 2004/0260333 to Dubrul et al. published on Dec. 23, 2004 ("Dubrul V") and U.S. Pat. Pub. No. 2010/0030256 to Dubrul et al. published on Feb. 4, 2010 ("Dubrul VI") describe a collection of funnel catheters, catheter/dilator assemblies, occluders, and associated methods which either entirely block blood flow or do not allow a controlled, predictable adjustment of allowed blood flow.

The prior art catheters and methods of use do not provide a minimal-trauma device that enables predictable and adjustable blood flow through or around a catheter device, prevent reflux as desired, allow centered and/or directional flow of medicament, or accurate, reliable and stable precise positioning. The device and method of the current invention described below addresses these deficiencies and problems, and further solves the problem of catheter tip instability which may result in infusion of a toxic agent unintentionally into surrounding vessels while preventing reflux from the desired vessel into the surrounding vessels and tissues even when the catheter tip is stable and other factors cause the toxic substance to reflux.

SUMMARY OF THE INVENTION

Certain embodiments of the present disclosure relate to a catheter with an anchoring device to stabilize the catheter tip when in use, such as when infusing, injecting, or delivering substances, devices or other catheters into a patient. The device is comprised generally of a tubular member configured as a catheter with a distal end comprising an outer sheath or tube, an inner sheath or tube, an anchoring mechanism such as a braid with permeable and impermeable portions that enables reliable and stable positioning of the catheter while delivering medicaments (or medical devices or implements such as stents) while allowing a controllable level of blood flow and/or reflux. Other embodiments and alternatives to this device are described in greater detail below.

As used in this disclosure, the terms "catheter", "anchor catheter", and "device" all refer to one or more embodiments of the invention.

By way of providing additional background, context, and to further satisfy the written description requirements of 35 U.S.C. §112, the following references are incorporated by reference in their entireties for the express purpose of explaining the nature of the catheter technology and surgical procedures in which catheters are used and to further describe the various tools and other apparatus commonly associated therewith: U.S. Pat. No. 5,078,685 issued to Colliver; U.S. Pat. No. 6,238,412 issued to Dubrul et al.; U.S. Pat. No. 6,695,858 issued to Dubrul et al.; U.S. Pat. No. 6,699,260 issued to Dubrul et al.; U.S. Pat. No. 6,635,068 issued to Dubrul et al.; U.S. Pat. No. 5,916,235 issued to Guglielmi; U.S. Pat. Pub. No. 2010/0114113 to Dubrul et al.; U.S. Pat. Pub. No. 2004/0260333 to Dubrul et al.; and U.S. Pat. Pub. No. 2010/0030256 to Dubrul et al.

According to varying embodiments described herein, the present invention is directed to the use of a catheter to any area of the body for administering medicaments or medical devices or implements such as stents. However, the invention may be used in any medical application where it is important to stabilize the distal end of a medical device. Also, the present invention may be used in primary surgery, as well as in revision surgery in which a follow-up procedure is being performed in an area that has previously been subject to one or more surgeries. Further, the invention may be used in any application where material is to be delivered with precision to a confined area where access is restricted, to include surgical procedures, repair of installed or uninstalled mechanical or electrical devices, and arming or disarming of explosive devices. Although many embodiments and example discuss use of the device within a human, the device and methods of use may be used in any animal. Also, although many embodiments and examples describe use of the device within a blood vessel or other human vessel, the device and methods of use may be used in any body channel of a human or animal In addition, although blood is referenced frequently as the fluid involved with the device, any fluid present in a body channel is applicable to the invention.

Briefly, in one preferred embodiment of the invention, the anchor catheter device employs an expansile member on the tip of a catheter designed to anchor the tip and provide stability while maintaining flow in the vessel, and further to limit and direct flow beyond the catheter tip to obviate reflux. To achieve stability of the catheter tip, a porous tubular mesh braid is attached to the distal aspect of the catheter in one embodiment. It may be a self expanding braid or it may be controlled by actuator sheaths which will be subsequently described. The braid expands to the vessel wall and stabilizes the catheter tip by contacting the wall, essentially anchoring it to the vessel wall by a gentle annular force.

According to the present invention, in one embodiment a catheter comprises an elongated catheter body having a distal end, a proximal end, and an axial lumen therebetween. The catheter also includes a housing having a hollow interior, an open proximal end, a distal end and an aperture on a lateral side of the housing. A coupling element is provided for connecting the distal end of the catheter body to the proximal end of the housing. A work element is movably disposed in the housing and operative through the aperture. A work element connector is disposed in a lumen of the catheter body, preferably the axial lumen, and has a distal end connected to the work element. The proximal end of the connector is available at the proximal end of the catheter body for attachment to a device appropriate for the operation of the work element.

According to various embodiments of the present disclosure, one aspect of the invention is to provide a catheter device that comprises a tubular member which is substantially hollow and that generally has a circular cross sectional shape. However, as one skilled in the art would appreciate, the device cross-section need not be limited to a generally circular shape. For example, cross-sections of an oval shape or those with at least one defined angle to include obtuse, acute, and right angles can provide a shape in some situations that is more congruent with the size or shape of the particular vessel area. A substantially round shape may also be employed that provides the surgeon with an indication of directional orientation.

According to various embodiments of the present disclosure, it is another aspect that the hollow tubular member further comprises a proximal end and a distal end, whereby the distal end is configured with an outer sheath or tube, an inner sheath or tube, a mesh braid with permeable and impermeable portions that enables reliable and stable positioning of the catheter while delivering medicaments (or medical devices or implements such as stents) while allowing a controllable level of blood flow and/or reflux. The inner sheath or tube fits within the outer sheath or tube. The method of use comprises precisely inserting the anchor catheter into the surgical area. The inner and outer sheaths are then engaged in a controllable manner to deploy an anchoring mechanism. In one embodiment, the anchoring mechanism is a mesh braid that is attached to one or both of the inner and the outer sheaths. When deployed, the mesh braid imparts a minimal but effective level of axial force against the surrounding vein so as to stabilize the catheter.

In one embodiment, the mesh braid is fitted with a portion that is impermeable to flow and a portion that is permeable to blood flow, therein controllably allowing blood flow through the vessel, in addition to controllably allowing reflux, or backflow, of medicament of other substances past the catheter tip.

In another embodiment, the device has the general shape of a standard selective angiographic catheter used to access abdominal vessels including the proper hepatic artery. The distal tip of the device however is comprised of an expansile mesh braid. The catheter comprises an outer sheath coaxially placed over an inner sheath. The two sheaths are moveable relative to the each other serving to expand and collapse the braid.

In further embodiments, the device includes a locking mechanism rotatably or otherwise attached to the outer sheath which may be fixable to the distal aspect of a hub of the device. When the braid of the device is expanded, the inner sheath is advanced into and through the outer sheath causing the locking mechanism to engage the distal aspect of the hub. The two components can be locked together by turning them or by other means. The device may be utilized alone or may be delivered through a guide catheter to the celiac axis. The guide catheter may in fact have the same or similar shape and features as the configuration demonstrated for the infusion or delivery catheter. The guide catheter, for example, may be anchored in the proximal celiac axis, and the infusion or delivery catheter would pass coaxially through the guide catheter.

In another embodiment of the invention, the braid of the device is bonded to the distal ends of an inner member and of an outer member. The braid is collapsed by withdrawing the inner member with respect to the outer member and expanded against the vessel wall by advancing the inner member with respect to the outer member. When expanded against the vessel wall, the braid will anchor the catheter tip and prevent it from moving because of patient movement, respiratory movement, or just because of the torque caused by the circuitous path traversed from, for example, the femoral artery to the proper hepatic artery. This will add significantly to the safety profile of the procedure. Moreover, an impermeable elastomeric membrane may cover a portion of the mesh braid so that antegrade blood flow occurs about and beyond the catheter tip, but the flow is partially obstructed or limited. This would cause the pressure in the hepatic arteries, for example, distal to the catheter tip to be less than the pressures proximal to the catheter tip, hence the likelihood of any reflux of infused agent would be markedly diminished. The elastomeric membrane may be placed on or within the mesh braid at any location to include near the inner member or near the outer member or in the middle, but preferably only covering a portion of the braid so that flow is maintained. In a preferred embodiment, the elastomeric membrane is placed on or within the mesh braid away from the catheter tip. This forces the blood to flow through the open portion of the braid and just distal to the tip of the catheter. This redirected flow insures enhanced admixing of the injected agent with the flowing blood. This feature is particularly important, for example, in the proper hepatic artery (which is a rather short artery) and it insures successful perfusion of both right and left hepatic artery branches.

Therefore, by incorporating the expansile mesh braid into the catheter tip, the current invention provides stability of the anchor catheter device preventing it from becoming dislodged from its position in, for example, the proper hepatic artery, and provides for back flow or reflux prevention by partially occluding the vessel while still providing for antegrade flow of blood that will carry the infused agent into the liver and to the tumor it is intended to treat. Enhanced admixing of the agent insures proportionate delivery of the agent to the branching arteries, especially if anchor catheter tip is positioned in close proximity to the arterial branches. It is usually desirable to place an anchor catheter tip in close proximity to the arterial branches to prevent the reflux phenomenon described above, therefore this flow directing feature of the current invention is quite desirable.

In an alternative embodiment, the expansile anchor of the anchor catheter device is configured as a mesh braid, yet is mounted solely to an inner sheath and not additionally mounted to an outer sheath. In this embodiment, the expansile anchor is an extension of the distal aspect of the inner sheath. When undeployed, the expansile anchor braid is within the lumen of the distal tip of the device and is internal to the outer sheath. The expansile anchor braid is extended or deployed by movement of the inner sheath away from or distally to the outer sheath. The expansile anchor braid self-deploys as the inner sheath is moved further away from the outer sheath; the expansile anchor braid deploys so as to rest against the vessel wall and impart a controlled axial force against the vessel wall. The expansile anchor braid is configured with a permeable mesh braid portion and an impermeable elastomeric portion. To control blood flow and pressure distally, the outer sheath is advanced over the permeable mesh braid portion, therein covering at least a portion of the permeable mesh braid portion and thus regulating or throttling blood flow. This embodiment may provide additional flexibility to the anchor catheter device.

In another embodiment, the coating of the tubular braid is placed in such a position that when the pressures distal to the tip become close to or equivalent with the pressures proximal to the tip, the extruded tubular braid changes shape somewhat so that even less blood flows through the permeable portions of the tubular braid.

In one embodiment, the device and all of its components are made of the same material. In another embodiment, the device and its components are made of different materials, for example, the inner and outer sheaths are made of one type of material, and the anchor braid is made of another material.

In one embodiment, the anchor mechanism does not employ an inflatable balloon or similar structure that confines a fluid within a closed space to achieve an anchoring function.

In one embodiment, the tubular braid is not a balloon as employed in catheters in the prior art that feature a balloon.

In one embodiment, the mesh braid is fitted with a membrane entirely impermeable to flow. Such an embodiment would be particularly useful after passing a stent delivery catheter through a lesion and deploying the stent, wherein the operator may want to aspirate the debris that is present to protect the downstream vasculature. In such a configuration, the device would serve as both an anchoring catheter and a proximal embolic protection catheter.

In another embodiment, a separate flap mechanism may be provided that would tend to allow forward flow but not reverse flow or reflux. The flap mechanism extends from within the inner sheath in a generally fluted-shape, ending in a fluted-bell, that extends past or distally to the distal tip of the device such that when extended, it has minimal to no effect on the blood flow in the vessel, but when rested against the expansile braid, restricts or totally prevents blood flow. The fluted-shape may be either of one continuous material or consist of a plurality of fans so as to, in totality, form a fluted-shape, either by overlapping with one another or through fitting without overlapping. The flap mechanism may be configured as other than a fluted shape, to include a conical shape. The flap mechanism may be configured as a flower with a plurality of petals. Further, the flap mechanism may be manipulated and/or deployed/retracted in any of several ways, to include as an additional, third sheath inner to the inner sheath, or as an integral part on the inner sheath. Further, the flap mechanism acts as a check value and is a passive device, wherein the flap mechanism prevents or occludes reverse flow yet allow antegrade that is forward flow.

In another embodiment, to further prevent movement or migration of the device during infusion, an attachment mechanism secured to the catheter shaft at or near the skin insertion site may be provided. It may vary in configuration from a suture attached to the tissues, to a clip at the skin level, to an anchoring device, or any other means of preventing movement of the catheter.

In one embodiment, the anchor mechanism is configured with an adhesive mechanism to provide additional stability of the device. For example, the adhesive mechanism may comprise striations, gripping surfaces, or an adhesive material.

In one embodiment, the anchor mechanism is configured with a mesh comprised of materials of variable strength, to include a mesh with elastomeric elements and elastomeric longitudinal elements. Further, the mesh may be of various fabric materials.

In other embodiments, the expansile tip of the anchor catheter that secures the catheter tip to the wall of the vessel while preserving flow beyond the catheter tip is accomplished through other means than a braided mesh structure, including, but not limited to stent like structures, parallel wires, non parallel wires, spiral elements, circular elements, tubular elements, laser cut structures, buddy wires, a malecot device, and any structure or component which expands near the distal tip of the catheter and secures it while preserving flow is included by this mention. Further, the expansile tip may be of any shape that is extendable or deployable to engage a vessel wall and impart axial pressure against a vessel wall, to include funnel shapes, umbrella shapes, conical shapes, and ring shapes.

In another embodiment, a catheter apparatus comprises a catheter body having a proximal portion, the distal portion having an expansile anchor mechanism operatively associated therewith, the anchor mechanism comprising mesh material at least at said distal portion that permits fluid to flow therethrough, the anchor mechanism having a first unexpanded configuration and a second expanded configuration, said second expanded configuration bringing said anchor mechanism into contact with a wall of a body cavity to reversibly anchor the distal portion of said catheter body in said cavity without substantially precluding a flow of fluid within said body cavity. This embodiment may further comprise a multi-petaled member connected to said distal portion that, when the anchor mechanism is in the second expanded configuration, the multi-petaled member substantially prevents the flow of fluid. Also, this embodiment may further comprise an anchor mechanism that, when in the expanded configuration, has a balloon-like shape but is devoid of any structure to confine a fluid.

In another embodiment, a catheter apparatus comprises a first tubular member comprising a first distal end and a first lumen; a second tubular member comprising a second distal end and a second lumen, said second tubular member received within the first lumen of the first tubular member; and a collapsible anchoring element adapted to be disposed within a body cavity across a passage thereto, said anchoring element having a collapsed shape and an extended shape, said collapsed shape being generally collapsed longitudinally along an axis of said second tubular member and expanded generally radially outwards therefrom to anchor said catheter against said body cavity; said first and second tubular members being connected to each other at their distal ends, and said first and second members being longitudinally movable relative to one another to control the movement of the anchoring element between the collapsed and extended shapes. This embodiment may further comprise an anchoring element that comprises a mesh. This embodiment may further comprise an anchoring element comprises an elastomeric.

The methods of utilizing all of the above configurations are quite similar. In the case of infusion of a substance into the liver and recovering the effluent venous blood, filtering out the toxic agent, and returning it to the body as has been previously described, imaging studies such as CT scans, MRI, or others are utilized to measure the distance between the most cephalad placement of the venous recovery catheter, whether it be the cavoatrial junction or the supradiaphragmatic IVC, and a point just above the renal veins. Measurements are also taken of the dimensions of the IVC. An appropriate sized recovery device is chosen. A catheter is placed in the proper hepatic artery from a femoral puncture for subsequent perfusion of the liver by a concentrated high dose substance. This infusion catheter is usually delivered to the celiac trunk by a guide catheter which may have a special shape for engaging the celiac axis or trunk. It may be the guide catheter described or a standard guide catheter. Further, the anchor catheter may be used as a guide catheter. In many cases, the anchor infusion catheter described above may be used as the infusion catheter. It is advanced through the guide catheter, through the celiac axis or trunk, and through the common hepatic artery, and the tip placed in the proper hepatic artery. In the case of the anchor catheter, the mesh anchor is deployed stabilizing the catheter tip. The mesh anchor may or may not comprise a partial elastomeric coating which limits flow past the catheter tip as described previously. The recovery device of the current invention, in one configuration or the other, is placed in the IVC and deployed so that the isolation apparatus covers the hepatic venous ostia and creates a hepatic venous effluent collection chamber. Testing is done to determine if the placement is appropriate by injection of contrast in a retrograde manner through the recovery catheter and into the hepatic venous effluent collection chamber, and demonstrating that there is no leakage from the isolated segment. Contrast is injected into the distal IVC to determine that there is good return through flow to the right atrium. Hepatic venous effluent will be collected, and the hepatic arterial infusion will begin through the hepatic artery infusion catheter. The venous effluent will be collected and pumped and filtered and returned as in the prior art devices for a period of time. After the arterial infusion is complete, the infusion catheter will be removed. In the case of the anchor catheter, the distal braid is collapsed by advancing the inner member with respect to the outer member. The venous effluent collection and treatment will continue for a prescribed period to prevent any delayed washout of the concentrated high dose substance from the liver into the systemic circulation. After a period of time, the chosen recovery device will then be collapsed, retracted, and removed from the body.

In one method of use of the anchor catheter device, a guide catheter configured with the anchor catheter device is placed coaxially over a diagnostic catheter. The diagnostic catheter is then utilized to catheterize the origin of the selected vessel, whether it be a coronary artery, a carotid artery, the celiac artery, or any other selected artery. The guide catheter of the current invention is then advanced over the tip of the diagnostic catheter to a point in the proximal selected artery. The anchor device of the current invention may then be deployed and the diagnostic catheter removed. The interventional catheter, whether it be a stent delivery catheter, an angioplasty catheter, atherectomy device, infusion catheter, or other type of catheter, will be advanced coaxially through the guide catheter of the current invention. In the case of tortuous anatomy in the selected artery, the anchored guide catheter of the current invention supports the advancement of the interventional catheter even down tortuous side branches and the like. This is of importance in accessing a point for infusion of a substance or for accessing a lesion distally placed in the selected artery. In the case of a stenotic lesion, the anchored guide catheter of the current invention supports the advancement of a guide wire through a narrow stenotic lesion, or even through a complete occlusion, and allows subsequent passage of the interventional catheter through a narrowed stenotic lesion. Forward pressure on the catheter will not cause it to dislodge the guide catheter of the current invention as that guide catheter is anchored securely within the orifice of the vessel. The problems with the prior art guide catheters are hence obviated, the lesions treated with less effort, less time, less cost, and less risk to the patient.

An additional use of the current invention includes capture of guide wires in any artery or vein, channel of the body, or tract or space whether natural or surgically created. In some other vascular interventions, it may be necessary to capture the tip of guide wire and to externalize the tip through a second puncture site. This can be accomplished with the current invention by placing the anchor catheter device into the artery, vein, or channel at a second and different location than the guide wire was initially placed. Expanding the braid of either embodiment will cause the end of the catheter to become somewhat funnel shaped. The guide wire can then be manipulated rather easily into the funnel shaped end of the catheter of the current invention, advanced toward the catheter hub, and advanced out of the catheter hub so that one end is entering the artery, vein, or channel at the original puncture site and the second end of the guide wire is exiting the second location. This may be important in performing thrombectomy in the venous system or in performing percutaneous stent graft placements in which at least a portion of to the stent graft is placed extraluminally, i.e., not within the artery, vein, or channel that is being bypassed, or in treating CTO's.

The device and method of the current invention will also solve the problem of catheter tip or guide catheter tip instability in other endovascular interventions in the carotid, coronary, renal, celiac, mesenteric and other arteries and veins. There are significant problems that can result from these iatrogenically created complications such as damage to the adjacent or distant organs and tissues and systemic effects that may create a cascade of events which result in stroke, myocardial infarction, infections, unnecessary surgery, and death among others. These complications are the result of the use of the standard angioplasty catheter for delivery of the agent or interventional device.

It is a purpose of this patent application to provide a new device or devices that will successfully and effectively deliver the concentrated agent or interventional device to the organ of interest without any reflux or flow into the surrounding adjacent vessels. Specifically, in the case of focal organ perfusion, the delivery of the agent will be only to the liver or other organ of interest by stabilizing the catheter tip with a novel catheter tip stabilization device, and prevent unintended reflux of the agent even when the catheter tip is stable by controlling the flow and pressures distal to the tip of the device. It is also a purpose of the current invention and method to facilitate the safe and effective delivery of interventional devices for endovascular treatments by enhancing the stability of the catheter tip.

In the case of a guide catheter which delivers a second diagnostic or interventional catheter coaxially through the lumen of the guide catheter, the catheter tip would be centered within the orifice of the catheterized artery by the stability device rather than the usually eccentric position of the tips of standard prior art guide catheters. This is a secondary benefit, but an important one. The guide catheter would be centered and anchored to the proximal portion of the artery catheterized, allowing the interventionalist to more easily pass other guide wires, catheters, and therapy devices distally into tortuous or partially occluded arteries. The likelihood of the guide catheter becoming dislodged from the vessel because of forward advancement pressures would be greatly diminished if not completely obviated. This stability of the tip of the guide catheter that prevents movement of the tip is a main function of the current invention. Other catheters could be inserted through this guide catheter even if the anatomy was problematic, such as an elongated aortic arch, or the distal vasculature was problematic from tortuosity or because of a stenotic lesion that resisted crossing. A catheter utilizing an expandable tubular mesh braid could also be utilized to deliver coils to occlude a vessel, or other substances or structures, especially if the vessel to be treated was not a subselective catheterization.

In the case of an infusion catheter, the current invention would secure the catheter tip within the artery and prevent it from becoming dislodged by patient motion, respiratory motion, pulsations within the artery, because of the torque on the catheter secondary to the circuitous route of the catheter or a combination of the above. One embodiment would utilize a tubular mesh braid to expand against the wall of the artery to be infused. This would prevent dislodgement. Further, a portion of the mesh braid in another embodiment would be covered with an impermeable elastomer that would permit blood flow around and distal to the catheter tip but limit the amount of flow. It would produce a partial obstruction to blood flow in the vessel. By limiting the flow, there would be enough blood flow maintained to carry the infused or injected substance distally into the branches of the artery and to the tumor, but the pressure distal to the catheter tip would be less than proximally so that the chance of reflux would be minimized if not obviated. Moreover, the elastomeric material is arranged in such a way to direct flow to the artery just distal to the catheter tip so that admixing of blood and the injected or infused substance is enhanced. This is accomplished by coating the portion of the tubular mesh braid that contacts the wall and a portion of the most distal tubular mesh braid but leaving the braid adjacent to and surrounding the catheter tip open. Even further, the construction of the braid and the coating may comprise elements that regulate the flow depending on pressure differences. Hence the current invention with an elastomeric coating placed at a specific location on the mesh braid will secure the tip in place, limit the flow to reduce or eliminate reflux, and enhance the admixture of blood and the injected substance.

One aspect of the present invention is directed to provision of a catheter that is able to achieve many of the functions of existing balloon catheters, but without the problems associated therewith. For example, in late 2010, the FDA has issued a class I recall—the agency's most serious—for a dilation catheter because the device may crack or break, which can result in bleeding or death. Cracks or breaks in the shaft of a Dilatation Catheter—used to dilate arterial stenoses—presented an issue where there was a risk that the balloon may fail to inflate or deflate, leading to unplanned intravascular or open surgery, significant vasospasm, prolonged tissue ischemia, tissue injury, infarct, bleeding, and/or death. As the present invention does not employ a balloon to achieve desired anchoring within a blood vessel, such issues are avoided.

The present invention further avoids many issues associated with prior art systems and methods, especially those that employ balloon catheter-type systems. For example, with respect to balloon catheter systems, there are problems in creating an accurate and repeatable process for pleating and folding long length balloon catheters (up to 250 mm) with the smallest possible profile. Prior art system have issues with the balloon profile, deployment characteristics and ability to re-fold upon deflation may differ greatly from unit to unit. Hand folding of such devices or mechanized folding and pleating systems still require a custom sizing of pleat head to the product specifications to create optimized folded balloons with the smallest profile with good deployment and re-fold characteristics. Prior art designs require that for one to achieve a desired balloon dimension, various process parameters must be attended to, such as but not limited to: diameter, temperature, balloon pressure/vacuum and delay/dwell times, all of which must be accurately controlled and subject to machine repeatability. With pleated balloon systems, it is desirable to have each pleat identical to allow for a uniform expansion. Once deflation is initiated the pleats of the balloon material must have sufficient re-fold characteristics to allow the balloon to fold at the locations previously imparted in the material allowing for a low extraction profile. All of these issues are avoided by the present invention.

Furthermore, with prior art catheter systems used for bladder issues, the tip of the catheter placed into the bladder has an inflatable "balloon" on the tip, which when inflated prevents the catheter from slipping out. In some cases, the balloon can tear or break while the catheter is being inserted through the urethra into the bladder. In other situations, the balloon may fail to inflate. Such issues are avoided by use of the present system and method as no inflatable balloon is employed.

Anchoring is achieved in an entirely distinct fashion that avoid the problems experienced with prior art balloon systems.

Another aspect of the present invention includes providing an anchor catheter device which is entirely or partially disposable. The outer sheath, inner sheath, and expansile anchor may comprise at least portions of biocompatible material which can stay in the vessel without impairing the final implantation. Alternatively, it may thus be a material that is resorbable, such as a resorbable polymer, in the vessel after the surgical procedure.

In another embodiment of the invention, the distal end of the anchor catheter device is in communication via a conduit to enable electrical, hydraulic, pneumatic, or mechanical transmission, the later such as a wire. Such hydraulic communication allows, for example, remote or automated use of the device. Such mechanical communication allows, for example, the distal end to be maneuvered with further precision.

It is yet another aspect of the present disclosure to provide an anchor catheter device that contains one or more detachable components. According to various embodiments, these detachable devices may include the expansile anchor or, for example, a medical device for implantation, such as a stent.

Furthermore, the anchor catheter may be configured to engage with other medical devices, such other medical devices to include other catheters. For example, in another embodiment of the invention, the anchor catheter may be attached to the exterior of a long teen indwelling central venous catheter to anchor the catheter within the soft tissue tunnel as will be subsequently described. It will not only stabilize the long term central venous catheter, but will block the tunneled tract or channel so that there is no ingress of bacteria that may cause infection.

One skilled in the art will appreciate that the distal end of the anchor catheter device need not be limited to those specific embodiments described above. Other forms, shapes or designs that enable the foregoing aspects of the present invention are hereby incorporated into this disclosure. Forms, shapes and designs that relate to the provision of an end of an anchoring device fitted to a catheter to perform medical procedures are considered to be within the scope of the present disclosure.

One of ordinary skill in the art will appreciate that embodiments of the present disclosure may have various sizes. The sizes of the various elements of embodiments of the present disclosure may be sized based on various factors including, for example, the anatomy of the patient, the person or other device operating the apparatus, the catheter insertion location, the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The anchor catheter elements could be flexible, semi-rigid, or rigid and made of materials such as stainless steel, titanium alloy, aluminum alloy, chromium alloy, and other metals or metal alloys. In certain embodiments, the anchor catheter and/or particular components are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the anchor catheter and/or particular components are made of a substantially transparent material and/or are rigidly opaque.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the stability and reliability speed of the procedure, the minimally invasive aspect of the procedure, the ability to controllably introduce medicaments (or medical devices or implements such as stents) to a site with minimal risk and damage to the surrounding tissue, the lower risk of infection, more optimally placed medicaments, and fewer tools in a vessel site due to the integration of several components required to provide or deliver medicaments to a receiving area. Further, the prior art does not provide a minimal-trauma device that enables predictable and adjustable blood flow through or around a catheter device, prevent reflux as desired, allow centered and/or directional flow of medicament (or medical devices or implements such as stents), or accurate, reliable and stable precise positioning. The device and method of the current invention addresses these deficiencies and problems, and further solves the problem of catheter tip instability which may result in infusion of a toxic agent unintentionally into surrounding vessels while preventing reflux from the desired vessel into the surrounding vessels and tissues even when the catheter tip is stable and other factors cause the toxic substance to reflux.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. Further, the drawings of the device do not detail all features of the device, and do not show the entire device, for example some drawings only detail the device end, and not the entire device length. Similar, some drawings do not detail the entire length of the channel involved, for example do not show the entire blood vessel length. It should be understood, of course, that the disclosure is not necessarily limited to the particular embodiments illustrated herein.

DETAILED DESCRIPTION

Figure 1:
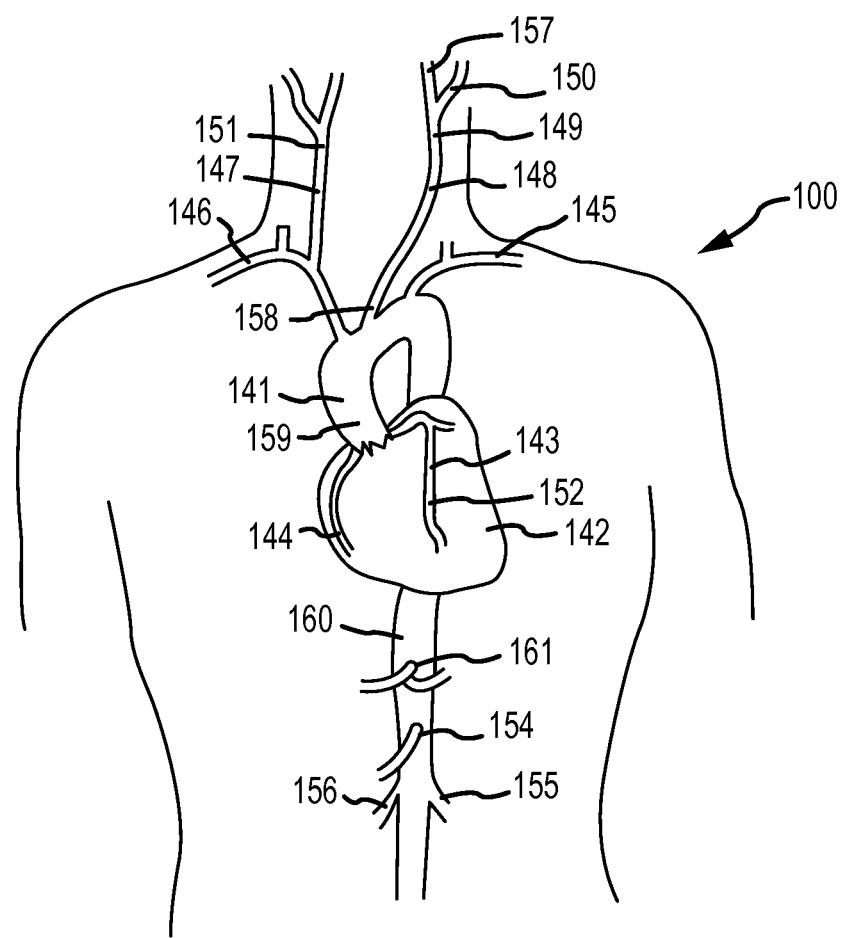
FIG. 1 schematically illustrates patient anatomy to include surgical points of interest.

The present invention relates to a catheter with an anchoring device to stabilize the catheter tip when in use, such as when infusing, injecting, or delivering substances, devices or other catheters into a patient. Thus, for example, the foregoing description of the various embodiments contemplates the use of an expansile member on the tip of the anchor catheter which is designed to anchor the tip and provide stability while maintaining flow in the vessel, and a novel configuration of this member will limit and direct flow beyond the catheter tip to obviate reflux. To achieve stability of the catheter tip, a porous tubular mesh braid is attached to the distal aspect of the catheter in one embodiment. It may be a self expanding braid or it may be controlled by actuator sheaths which will be subsequently described. The braid expands to the vessel wall and stabilizes the catheter tip by contacting the wall, essentially anchoring it to the vessel wall by a gentle annular force.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

In order to provide greater clarity to the embodiments of the invention, a detailed description of the utility of the anchor catheter device of the current invention is first provided. An example medical procedure detailed is that of infusing a substance into the liver, but one of ordinary skill in the art will appreciate the concepts are transportable to most any other artery. A utility is to anchor a guide catheter, delivery catheter and the like so that the tip of the anchored catheter is stable, does not move, and offers support for advancement of other devices, among other features.

Figure 2:
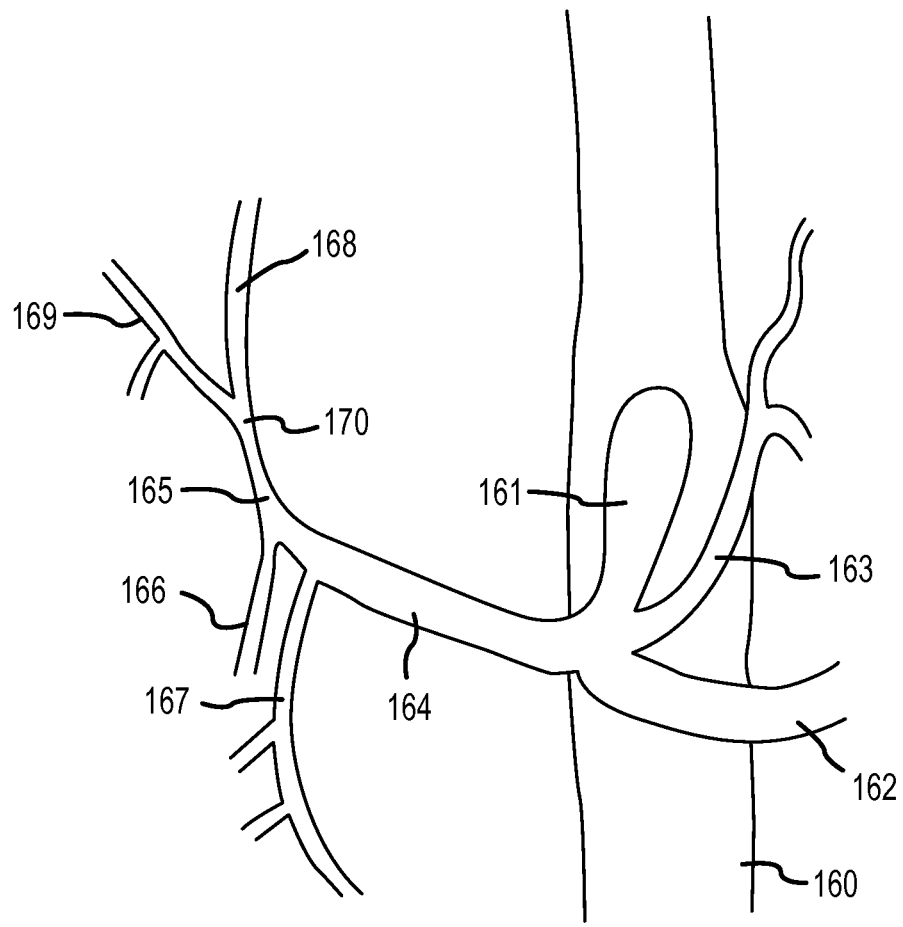
FIG. 2 schematically illustrates patient anatomy of the branches of the celiac axis.

Referring now to FIGS. 1-2, the anatomy of a patient is shown.

In regard to FIG. 1, patient anatomy is schematically illustrated to include surgical points of interest. FIG. 1 demonstrates organs and areas of interest within a patient 100, specifically the aorta 141, heart 142, right coronary artery 144 and left anterior descending coronary artery 143, right common carotid artery 147 and left common carotid artery 148 and other vessels, including the right 146 and left 145 subclavian arteries, celiac artery trunk 161, superior mesenteric artery 154, and right renal artery 156 and left renal artery 155. Of particular interest are the coronary arteries 143 and 144 and carotid arteries 147 and 148, which are frequently accessed for endovascular interventions such as stenting and angioplasty. One can appreciate the tortuous path that a catheter must take to be placed at catheter positioning point 149 in the left common carotid artery 147 prior to and during a stent placement at stent placement point 150 in the left common carotid artery 148. To facilitate the placement of a catheter (not shown) and the delivery of a stent (not shown) at this location, a guide catheter (not shown) is often utilized with the tip being placed at guide catheter positioning point 158. The aforementioned catheter and stent delivery device are placed coaxially within and through the guide catheter with tip at guide catheter positioning point 158 and then they are advanced to catheter positioning point 149 prior to the intervention. However, advancing the stent delivery device to catheter positioning point 149 frequently causes the guide catheter to back out of the origin of the left common carotid artery 148 and into the ascending aorta 141 preventing the proper placement of the catheter and stent delivery device at catheter positioning point 149. Even if the stent delivery catheter is successfully delivered to catheter positioning point 149, attempts to advance it through a stenotic lesion of stent placement point 150 will cause the guide catheter to become dislodged from its guide catheter positioning point 158 in the proximal left common carotid artery 148. This will necessitate repeated unsuccessful attempts to coax the stent delivery device across the lesion, a catheter exchange and time delays, prolonging the procedure and creating additional risk of stroke to the patient. As will be demonstrated subsequently, the current invention will secure the guide anchor catheter 171 to a point in the proximal left common carotid artery 148 and overcome the technical problems caused by frequently encountered tortuous patient anatomy and narrowed stenotic lesions that create resistance to the passage of guide wires and/or catheters.

Similarly, to access a point in the left anterior descending coronary artery 143, a guide catheter (not shown) is used and the tip is placed within the left main coronary artery 159 with the stent delivery catheter (not shown) placed coaxially though the guide catheter. Advancing a guide wire (not shown) or stent delivery catheter into the distal left anterior descending coronary artery 143 through a stenosis at stenosis point 152 which provides resistance can obviously be problematic because of the tortuous anatomy and the resistance caused by the stenotic lesion. Analogous to the above description, the tortuosity and the resistance caused by the stenotic lesion will cause the guide catheter to become dislodged from its purchase in the origin of the left main coronary artery 159. When the guide catheter becomes dislodged, there is no support to push the guide wire or stent delivery catheter through the stenotic lesion, and this necessitates multiple catheter and/or guide catheter exchanges, guide wire exchanges, further pre-dilatation of the lesion, and so forth that would not be necessary if the guide catheter were secured and offered support to the advancement of the guide wire or catheters through the stenotic lesion.

The same phenomenon of inability to properly access a vascular area or lesion occurs in many of the other arteries shown in FIG. 1. One of ordinary skill in the art is familiar with the specific difficulties involved in accessing individual arteries. These difficulties may occur when performing a vascular intervention such as angioplasty, stent placement, or the like, and when placing a catheter at a specific location for infusing an agent or substance among other reasons.

Furthermore, crossing chronic total occlusions (CTO's) deserves special mention as there is complete occlusion of the vascular lumen. Probing with the guide wire through the "cap" of the occlusion, or the hardened face of the occlusion, can be difficult with much resistance as there is no lumen. Typically, the guide wire causes the guide catheter or interventional catheter to back out of its position within the artery rather than exerting enough forward pressure to penetrate and pass through this arterial cap. By anchoring the current device to the arterial wall, more forward pressure will be exerted and the CTO will be more easily crossed. Moreover, the device of the current invention will center the catheter lumen, and hence the guide wire, in the center of the vessel. The penetration of the arterial cap will less likely result in a subintimal passage of the guide wire than if done with an eccentrically placed guide wire. Therefore, the passage through the CTO will be done more easily and within the correct channel than with prior art devices.

In regard to FIG. 2, anatomy of the celiac axis is schematically illustrated to include surgical points of interest. FIG. 2 presents the celiac artery 160, including the celiac trunk 161, the splenic artery 162, the left gastric artery 163 and the common hepatic artery 164. Further, the common hepatic artery 164 supplies the right gastric artery 167, the gastroduodenal artery 166, and the proper hepatic artery 165. The infusion catheter is usually placed through a puncture in the common femoral artery (not shown) in the groin, through the celiac trunk 161 and the common hepatic artery 164 and into the proper hepatic artery 165. The tip must be placed proximal to the origins of the left hepatic artery 168 and the right hepatic artery 169 so that the infused substance flows into each artery in generally the same concentration. The tip must be placed at approximately artery point 170 to accomplish this. One can appreciate the tortuous path that the catheter must take to reach this point from the groin especially considering the catheter must traverse many different planes not shown in this two dimensional drawing. Since there is some inherent stiffness in the catheter to enable maneuverability given the tensile forces imparted to the catheter, the multiple curving vessels causes some torque on the distal catheter creating potential instability of the tip, especially when the catheter is subjected to motion from breathing, arterial pulsations, or patient movement. One can also readily appreciate the close proximity of the right gastric artery 167 and the gastroduodenal arteries 166 to the proper hepatic artery 165, and realize that only minimal movement of the catheter tip may cause it to become dislodged from the rather short proper hepatic artery 165, allowing a toxic agent to be inadvertently infused into the left gastric 167 and gastroduodenal arteries 166 which supply the distal stomach, pylorus, duodenum, and pancreas or even more proximal arteries and the aorta. In fact, frequently the distance between the origin of the proper hepatic artery 165 and the artery point 170 proximal to the bifurcation of the proper hepatic artery 165 is only two (2) centimeters or less. Infusing a toxic substance into this small target area obviously can be risky not only from catheter movement, but also just from reflux of the infused material proximally into the other arteries, such as the gastroduodenal arteries 166, the right gastric artery 167 and left gastric artery 163, and the splenic artery 162, even if the catheter were stable.

Referring now to FIGS. 3-6, several embodiments of the present invention are shown.

Figure 3:
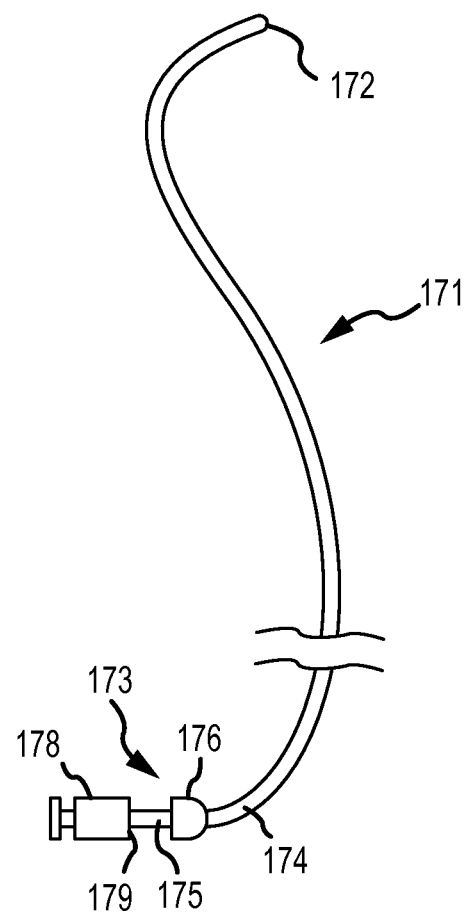
FIG. 3 provides a side view of one embodiment of the device including a distal portion fitted with an inner sheath, and outer sheath, a hub, and locking mechanism.

In regard to FIG. 3, an anchor catheter device 171 is shown comprising an anchor catheter proximal tip 172, an anchor catheter distal tip 173, an outer sheath or tube 174 and an inner sheath or tube 175. Each of the anchor catheter proximal tip 172 and the anchor catheter distal tip 173 form lumens. The device 171 has the general shape of a standard selective angiographic catheter used to access abdominal vessels including the proper hepatic artery 165 of FIGS. 1 and 2. The anchor catheter device 171 is configured to include a housing having a hollow interior, an open proximal end 172, a distal end or tip 173 and an aperture on a lateral side of the housing. A coupling element is provided for connecting the distal end 173 of the catheter body to the proximal end of the housing. Various work elements or mechanisms are mounted and movably disposed at the anchor catheter distal tip 173 and configured in the housing and operative through the aperture. A work element connector is disposed in a lumen of the catheter body, preferably the axial lumen, and has a distal end connected to the work element. The proximal end of the connector is available at the proximal end of the catheter body for attachment to a device appropriate for the operation of the work element.

FIG. 3 generally provides the embodiment of the anchor catheter device 171 in one embodiment particularly suited to perform as an infusion or delivery catheter. Alternatively it could represent a guide catheter to access the celiac trunk 161 of FIGS. 1 and 2. The device 171 has the general shape of a standard selective angiographic catheter used to access abdominal vessels including the proper hepatic artery 165 of FIGS. 1 and 2.

In the embodiment of FIG. 3, the device 171 includes a locking mechanism 176 rotatably or otherwise attached to the outer sheath 174 which may be fixable to the distal aspect of a hub 178 of the device 171. When an anchoring mechanism or work element, such as a braid, of the device 171 is expanded, the inner sheath 175 is advanced into and through the outer sheath 174 causing the locking mechanism 176 to engage the distal aspect of the hub 178. The two components can be locked together by turning them or by other means. The device 171 may be utilized alone or may be delivered through a guide catheter to the celiac axis. A companion guide catheter may in fact have the same or similar shape and features as the configuration demonstrated for the device 171 when used for infusion or delivery. A guide catheter, for example, may be anchored in the proximal celiac axis, and the device 171 would pass coaxially through the guide catheter to, for example, the artery point 170 of FIG. 2. The device 171 may also be fitted with a guide catheter to thus operate as a substantially integrated unit or device.

In the embodiment of FIGS. 4A-J, a preferred embodiment of the device 171 is provided in detail that comprises an expansile anchor 181 mechanism or working element which may be controllably deployed within a vessel wall 200 of a patient 100.

Figure 4A:
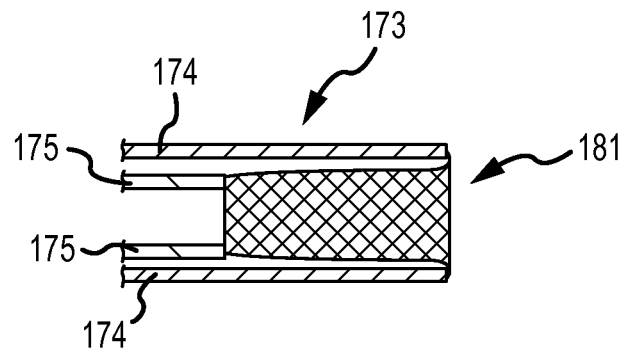
FIG. 4A is a cross sectional view of the distal tip of the device, the embodiment having fitted with an inner sheath, outer sheath, and undeployed expansile anchor.
Figure 4B:
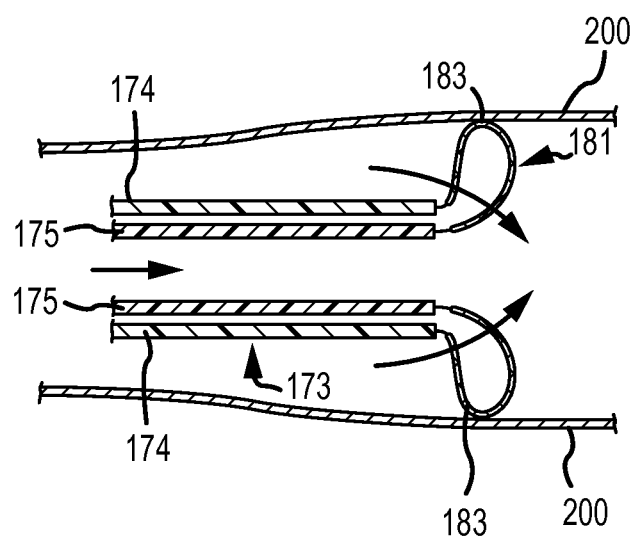
FIG. 4B is a cross sectional view of the distal tip of the device of FIG. 4A inserted within a vessel of a patient and the embodiment having an expansile anchor deployed, showing flow through the center of the device and around the exterior of the device through the expansile anchor.
Figure 4C:
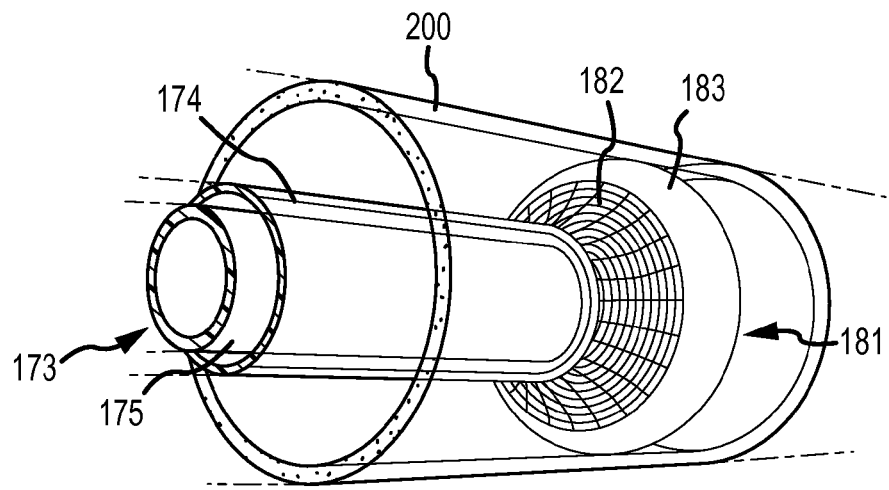
FIG. 4C is a perspective view of the distal tip of the device of FIG. 4A inserted within a vessel of a patient and with the expansile anchor deployed.
Figure 4D:
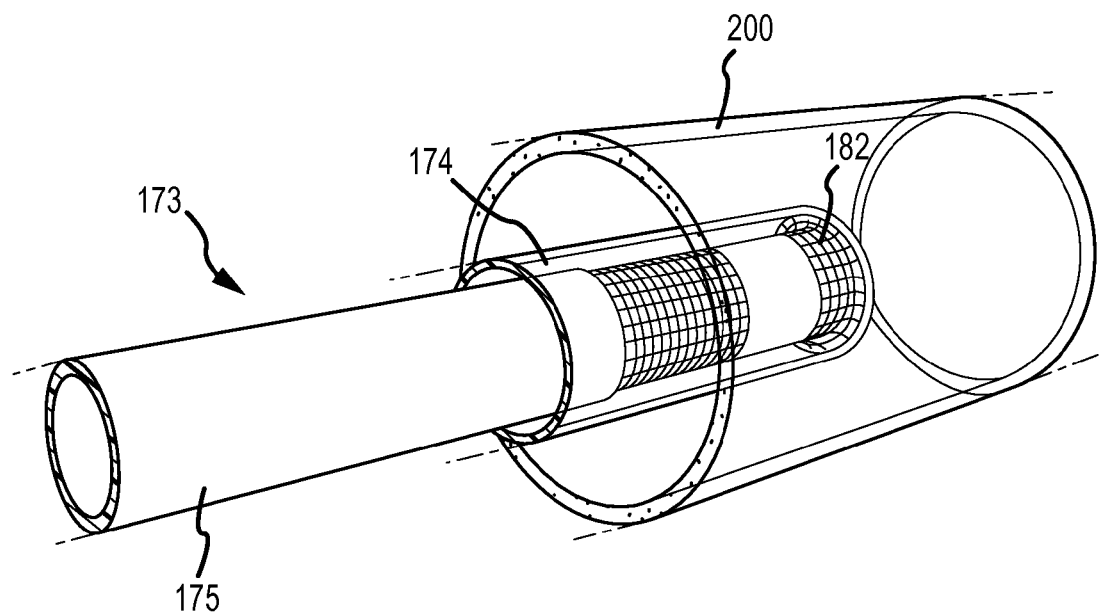
FIG. 4D is a perspective view of the distal tip of the device of FIG. 4A inserted within a vessel of a patient and with the expansile anchor undeployed.
Figure 4E:
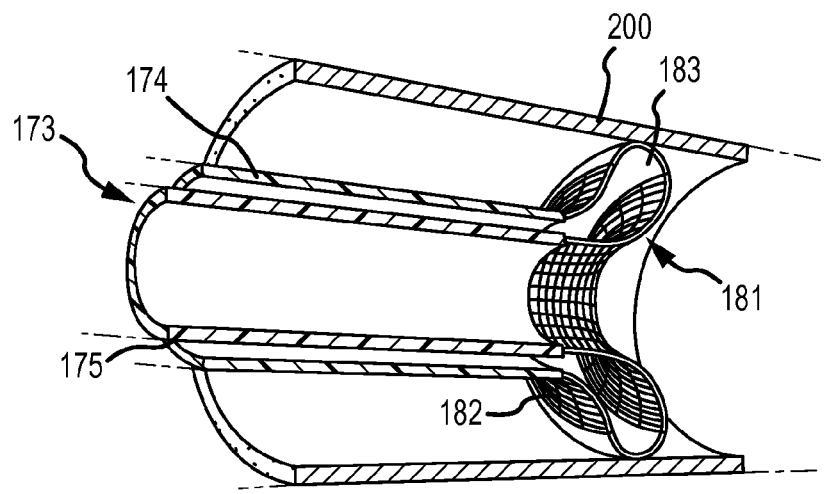
FIG. 4E is a cross-sectional, perspective view of the distal tip of the device of FIG. 4A inserted within a vessel of a patient and with the expansile anchor deployed.
Figure 4F:
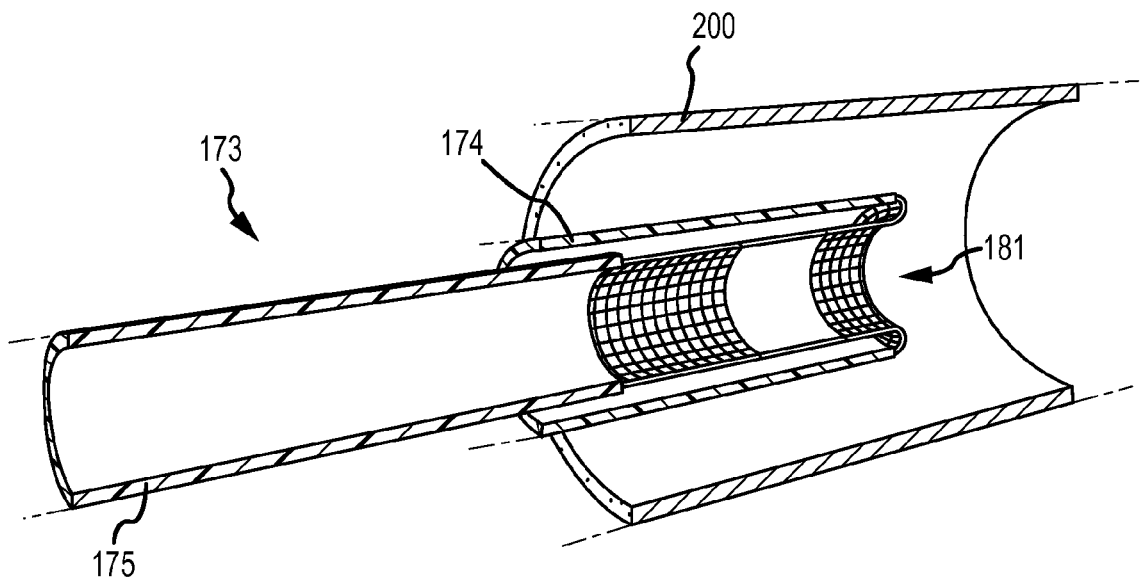
FIG. 4F is a cross-sectional, perspective view of the distal tip of the device of FIG. 4A inserted within a vessel of a patient and with the expansile anchor undeployed.
Figure 4G:
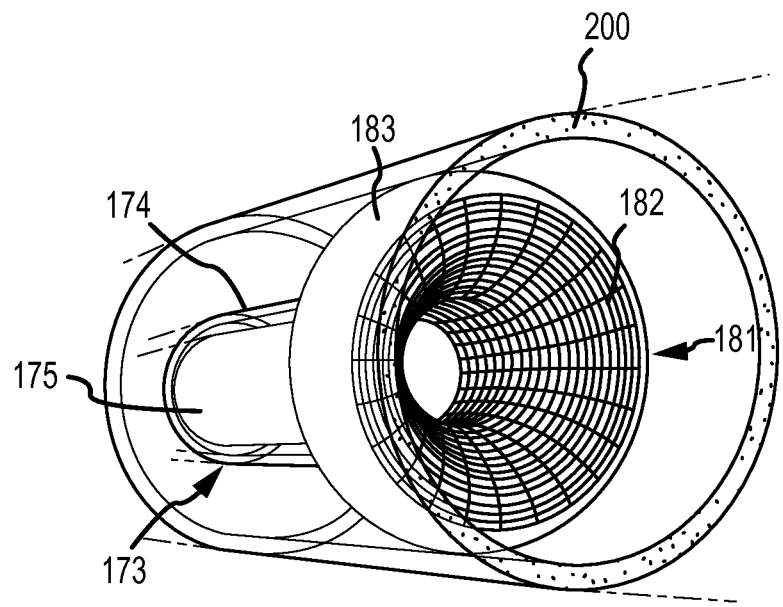
FIG. 4G is a perspective view of the distal tip of the device of FIG. 4A inserted within a vessel of a patient and with the expansile anchor deployed.
Figure 4H:
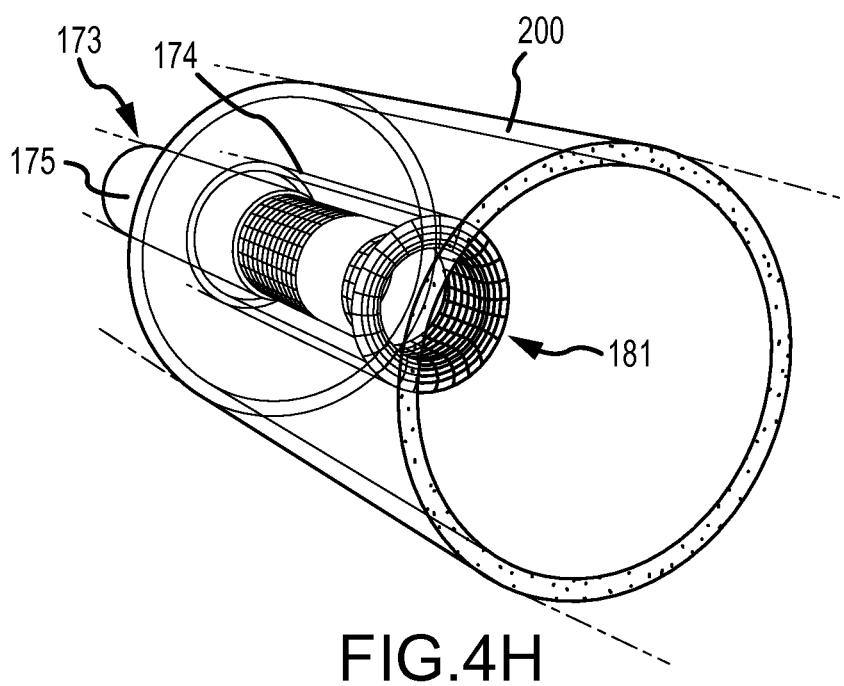
FIG. 4H is a perspective view of the distal tip of the device of FIG. 4A inserted within a vessel of a patient and with the expansile anchor undeployed.
Figure 4I:
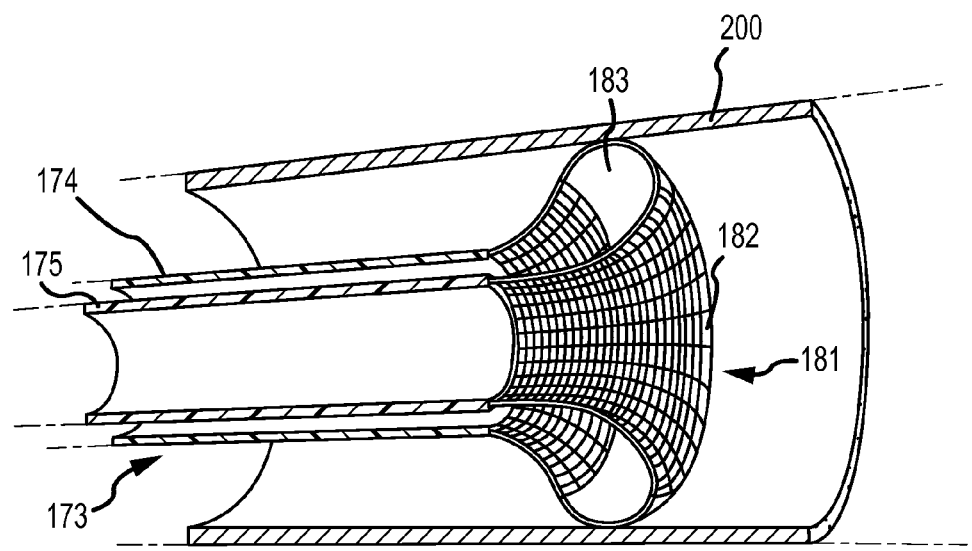
FIG. 4I is a cross-sectional, perspective view of the distal tip of the device of FIG. 4A inserted within a vessel of a patient and with the expansile anchor deployed.
Figure 4J:
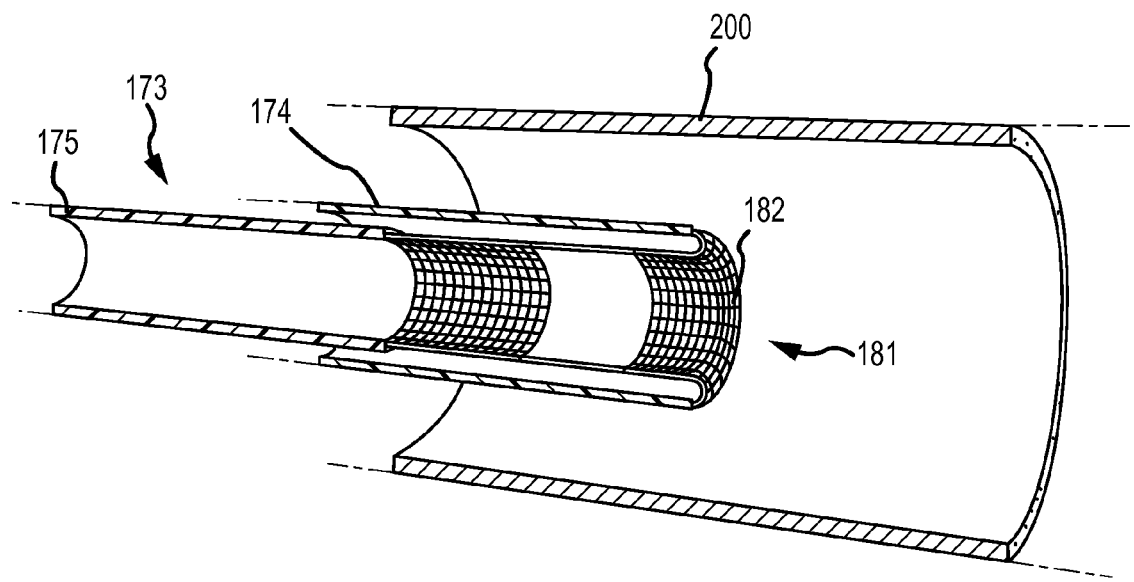
FIG. 4J is a cross-sectional, perspective view of the distal tip of the device of FIG. 4A inserted within a vessel of a patient and with the expansile anchor undeployed.
Figure 5A:
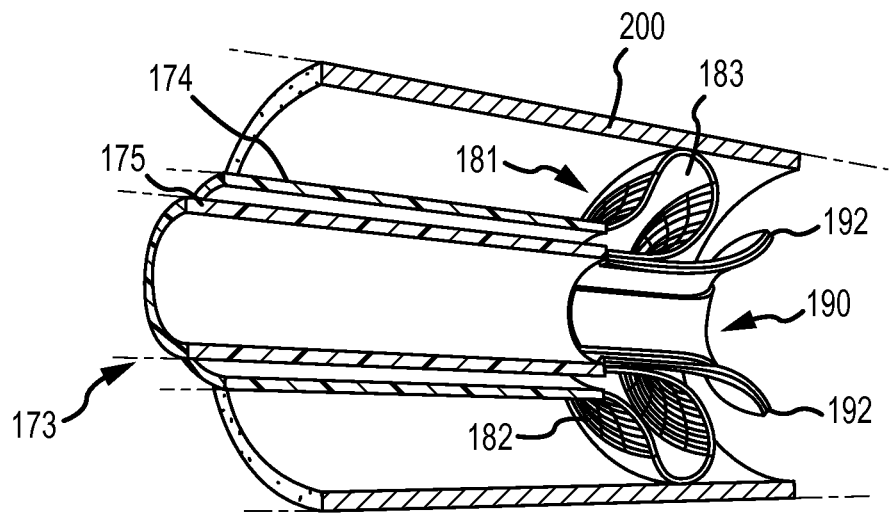
FIG. 5A is a cross-sectional, perspective view of the distal tip of an embodiment of the device inserted within a vessel of a patient, the embodiment having an expansile anchor deployed, and with flap mechanism deployed.
Figure 5B:
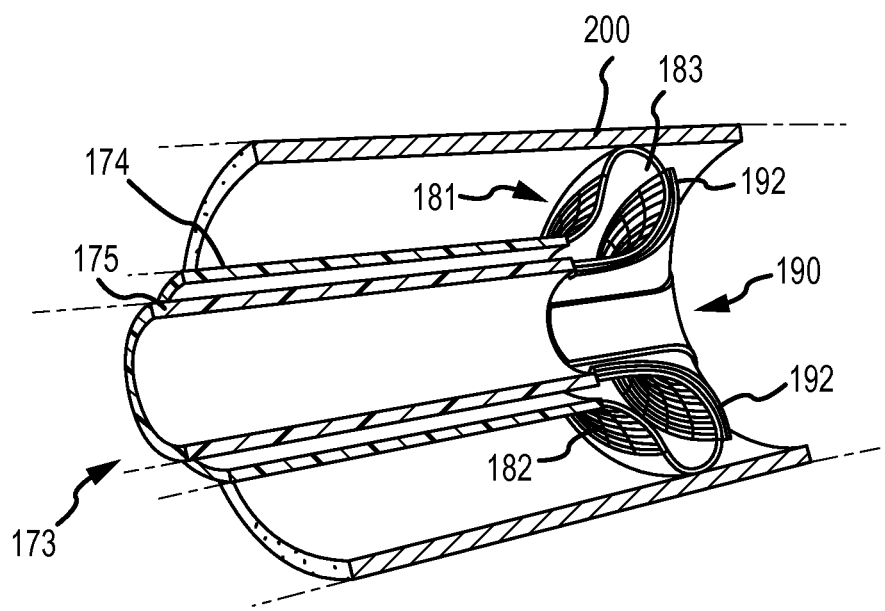
FIG. 5B is a cross-sectional, perspective view of the distal tip of an embodiment of the device inserted within a vessel of a patient, the embodiment having an expansile anchor deployed, and with flap mechanism deployed so as to conform to the deployed expansile anchor and thus prevent reflux.
Figure 5C:
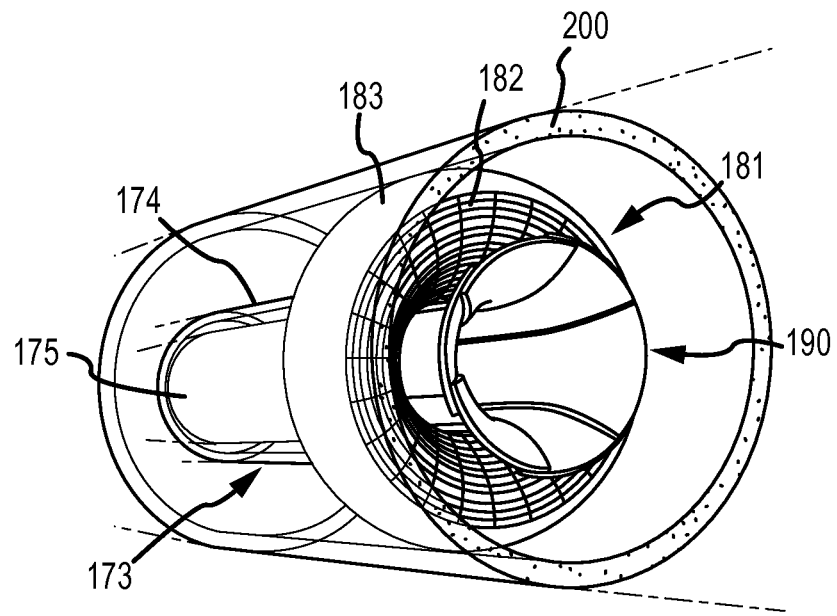
FIG. 5C is a perspective view of the distal tip of an embodiment of the device of FIG. 5A inserted within a vessel of a patient, the embodiment having an expansile anchor deployed, and with flap mechanism deployed.
Figure 5D:
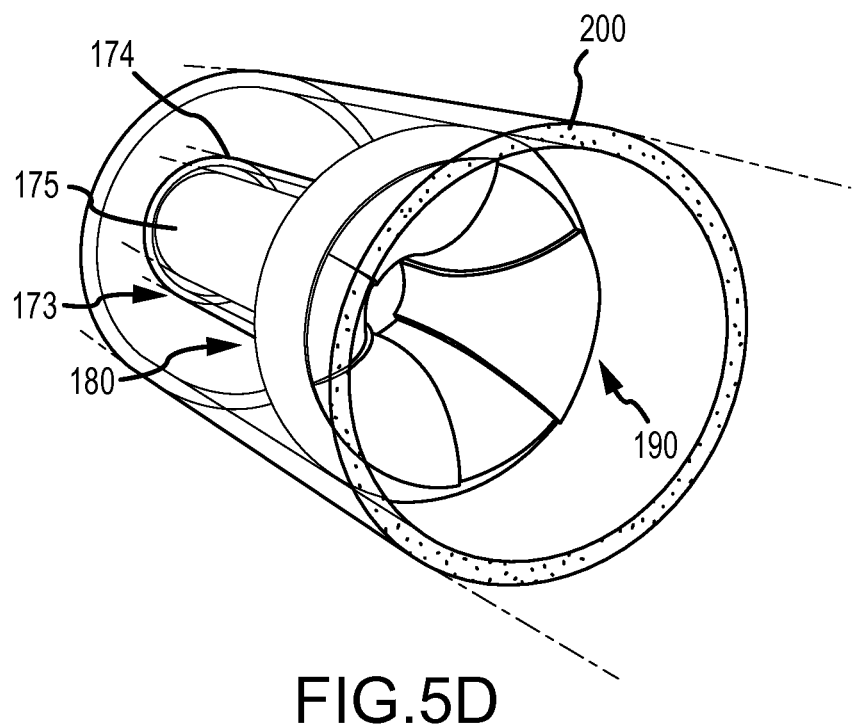
FIG. 5D is a perspective view of the distal tip of an embodiment of the device of FIG. 5B inserted within a vessel of a patient, the embodiment having an expansile anchor deployed, and with flap mechanism deployed so as to conform to the deployed expansile anchor and thus prevent reflux.
Figure 5E:
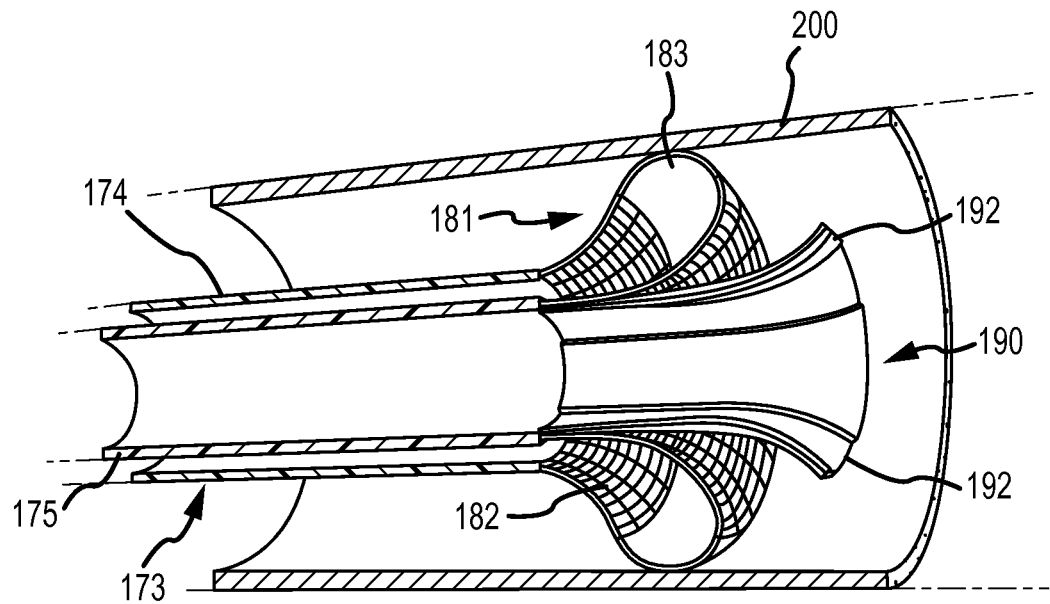
FIG. 5E is a cross-sectional, perspective view of the distal tip of an embodiment of the device of FIG. 5A inserted within a vessel of a patient, the embodiment having an expansile anchor deployed, and with flap mechanism deployed.
Figure 5F:
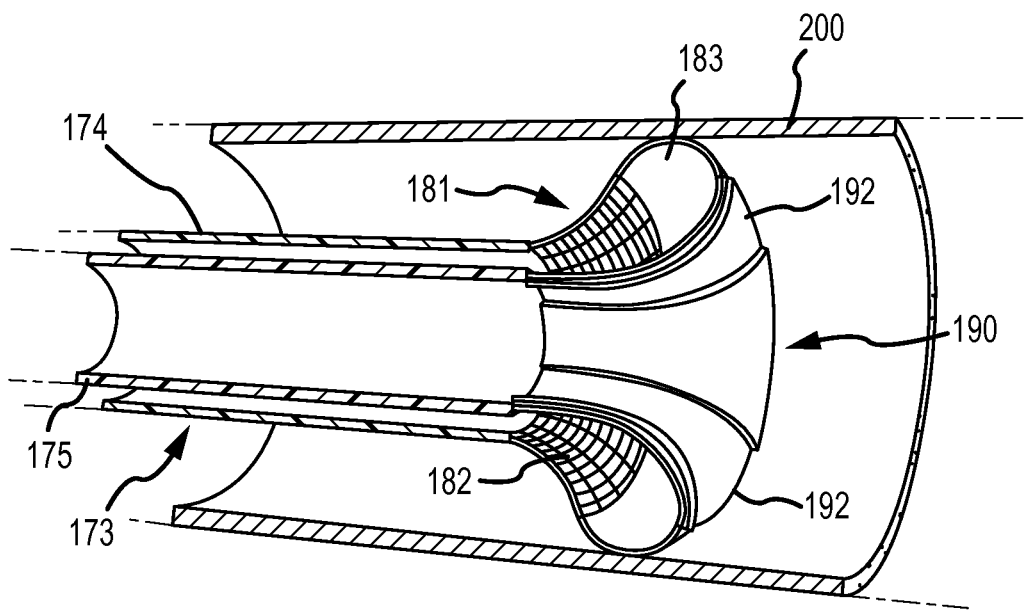
FIG. 5F is a cross-sectional, perspective view of the distal tip of an embodiment of the device of FIG. 5B inserted within a vessel of a patient, the embodiment having an expansile anchor deployed, and with flap mechanism deployed so as to conform to the deployed expansile anchor and thus prevent reflux.

Referring now in detail to FIGS. 4A-B, cross-sectional views of an anchor catheter device 171 is provided with a distal tip 173 configured with an expansile anchor 181. When deployed, the expansile anchor 181 imparts a minimal but effective level of axial force against the surrounding vessel 200 of a patient 200 so as to stabilize the anchor catheter device 171. The anchor catheter device 171 comprises an outer sheath 174 coaxially placed over an inner sheath 175. The two sheaths are moveable relative to the each other serving to expand and collapse the expansile anchor 181. FIG. 4A depicts the device 171 with the expansile anchor 181 undeployed, a configuration utilized when the device is inserted into the patient 100. Further, FIG. 4A-B depict the expansile anchor 181 configured as a mesh braid. When the braid is expanded, as depicted in FIG. 4B, the inner sheath 175 is advanced into and through the outer sheath 174 causing the expansile mesh braid 181 to controllably engage the vessel wall 200. Herein the terms "expansile anchor" and "mesh braid" and "braid" all reference the expansile anchor mechanism 181. The expansile anchor mechanism 181 may be a self-expanding or it may be controlled by actuator sheaths which will be subsequently described. The braid 181 expands to the vessel wall 200 and stabilizes the catheter distal tip 173 by contacting the vessel wall 200, essentially anchoring the device 171 to the vessel 200 wall by a gentle annular force.

In regard to FIG. 4B, the expansile mesh braid 181 on the tip of the device 171 is designed to anchor the distal tip 173 and provide stability while maintaining flow in the vessel 200, and further to limit and direct flow beyond the catheter distal tip 173 to obviate reflux. Medicament (or medical devices or implements such as stents) is delivered to the patient 100 through the inner sheath 174 of the device 171, as depicted by the center, left to right, arrow in the center of the device 171. In this manner, medicament flow is directed beyond the catheter distal tip 173 and minimizes backflow or reflux of the medicament. Harmful effects of uncontrolled or errant reflux was discussed in previously, and is to be avoided.

In the embodiment of the invention of FIGS. 4A-J, the expansile anchor or braid 181 of the device 171 is bonded to the distal ends of the inner sheath or tube 175 and to the outer sheath or tube 174. FIGS. 4C-J provide perspective views of the distal tip of the device of FIGS. 4A-B as inserted within a vessel 200 of a patient 100. FIGS. 4C, 4E, 4G, and 4I depict the expansile anchor 181 deployed, while FIGS. 2D, 4F, 4H, and 4J depict the expansile anchor 181 not deployed. The expansile anchor braid 181 is collapsed (i.e. moved from deployed to not deployed position) by withdrawing the inner sheath 175 with respect to the outer sheath 174 and expanded (i.e. deployed) against the vessel wall 200 by advancing the inner sheath member 175 with respect to the outer sheath member 174. When the braid 181 is expanded against the vessel wall 200, the braid 181 will anchor the catheter tip 173 and prevent the catheter tip 173 from moving because of patient 100 movement, respiratory movement, or just because of the torque caused by the circuitous path traversed from, for example, the femoral artery to the proper hepatic artery 165 of FIG. 2. This will add significantly to the safety profile of the procedure. Moreover, an impermeable elastomeric membrane 183 may cover a portion of the mesh braid so that antegrade blood flow occurs about and beyond the catheter tip, but the flow is partially obstructed or limited. This would cause the pressure in the hepatic arteries 168 and 169 of FIG. 2, for example, distal to the catheter tip 173 to be less than the pressures proximal to the catheter tip 173, hence the likelihood of any reflux of infused agent or medicament would be markedly diminished. The impermeable elastomeric membrane 183 may be placed on or within the mesh braid 181 at any location to include near the inner sheath 175 or near the outer sheath 174 or in the middle between sheaths 174 and 175, but preferably only covering a portion of the braid 181 so that flow is maintained. In this embodiment of the device 171, the expansile anchor 181 comprises an impermeable elastomeric membrane portion 183 and a permeable mesh braid portion 182, thereby providing a level of controllability to the blood flow, to include the blood flow between the device 171 and the vessel wall 200.

In delivering drugs, embolics, or other substances to tumors within organs, it may be important to control the flow to that organ for another reason. Usually the tumors within an organ are more vascularized than the normal tissue and flow is preferential to the tumors. This may cause greater blood flow in the artery serving the organ. By diminishing the overall blood flow to the organ, one may create a condition in which there is a exaggerated disproportionate flow of blood to the tumor or fibroid as the more highly vascularized tumor will siphon the blood flow from the normal tissues. This will allow more of a chemotherapeutic agent, embolic agent, other drugs and materials to be delivered to the tumor than to the normal tissues from a more remote catheter tip position within the main artery to the organ or a first branch of the main artery rather than a subselective or suprasubselective branch near the tumor. Hence control of the blood flow has advantages other than preventing reflux in that the agents to be delivered may be delivered more easily and timely.

In a preferred embodiment, the impermeable elastomeric membrane 183 is placed on or within the expansile anchor mesh braid 181 away from the catheter tip 173. This forces the blood to flow through the open portion of the braid 181 as demonstrated by the arrows of FIG. 4B and about and just distal to the distal tip 173 of the anchor catheter device 173. This redirected flow insures enhanced admixing of the injected agent or medicament with the flowing blood. This feature is particularly important in the proper hepatic artery 165 of FIG. 2 which is a rather short artery and it insures successful perfusion of both right and left hepatic artery branches 167, 168 of FIG. 2.

Therefore, by incorporating the expansile mesh braid 181 into the catheter tip 173, as depicted in FIGS. 4A-J, the current invention provides stability of the anchor catheter device 171 preventing the device 171 from becoming dislodged from its position in, for example, the proper hepatic artery 165 of FIG. 2, and provides for back flow or reflux prevention by partially occluding the vessel 200 while still providing for antegrade flow of blood that will carry the infused agent or medicament into, for example, the liver and to the tumor it is intended to treat. Enhanced admixing of the agent or medicament insures proportionate delivery of the agent to the branching arteries, especially if the anchor catheter tip 173 is positioned in close proximity to the arterial branches. Further, it is frequently desirable to place a catheter in close proximity to the arterial branches to prevent the reflux phenomenon described above, therefore this flow directing feature of the current invention device 171 is highly desirable.

In a further embodiment based upon that depicted in FIGS. 4A-J, the coating of the mesh braid 183 is placed in such a position that when the pressures distal to the tip 173 (i.e. to the right in, for example, FIG. 4B) become close to or equivalent with the pressures proximal to the tip (i.e. to the left in FIG. 4B), the mesh braid 183 changes shape so that a further reduction in blood flow occurs through the permeable portions of the tubular braid 183.

Referring now to FIGS. 5A-F, a further embodiment of the device 171 is provided in detail that comprises an expansile anchor 181 mechanism or working element which may be controllably deployed within a vessel wall 200 of a patient 100, as well as a flap mechanism 190 with flap mechanism fluted-bell 192. This embodiment is similar to that of FIGS. 4A-J, with the addition of the flap mechanism 190 and flap mechanism fluted-bell 192.

Referring now in detail to FIGS. 5A-F, perspective views are depicted of the anchor catheter device 171 as provided with a distal tip 173 configured with an expansile anchor 181. When deployed, the expansile anchor 181 imparts a minimal but effective level of axial force against the surrounding vessel 200 of a patient 200 so as, to stabilize the anchor catheter device 171. The anchor catheter device 171 comprises an outer sheath 174 coaxially placed over an inner sheath 175. The two sheaths are moveable relative to the each other serving to expand and collapse the expansile anchor 181. FIGS. 5A-F all depict the device 171 with the expansile anchor 181 deployed as inserted within a vessel 200 of a patient 100. To deploy the expansile anchor 181, the inner sheath 175 is advanced into and through the outer sheath 174 causing the expansile mesh braid 181 to controllably engage the vessel wall 200. The expansile anchor mechanism 181 may be a self-expanding or it may be controlled by actuator sheaths which will be subsequently described. The braid 181 expands to the vessel wall 200 and stabilizes the catheter distal tip 173 by contacting the vessel wall 200, essentially anchoring the device 171 to the vessel 200 wall by a gentle annular force.

In the embodiment of the invention of FIGS. 5A-F, the expansile anchor or braid 181 of the device 171 is bonded to the distal ends of the inner sheath or tube 175 and to the outer sheath or tube 174. The expansile anchor braid 181 is collapsed (i.e. moved from deployed to not deployed position) by withdrawing the inner sheath 175 with respect to the outer sheath 174 and expanded (i.e. deployed) against the vessel wall 200 by advancing the inner sheath member 175 with respect to the outer sheath member 174. Moreover, an impermeable elastomeric membrane 183 may cover a portion of the mesh braid so that antegrade blood flow occurs about and beyond the catheter tip, but the flow is partially obstructed or limited. This would cause the pressure in the hepatic arteries 168 and 169 of FIG. 2, for example, distal to the catheter tip 173 to be less than the pressures proximal to the catheter tip 173, hence the likelihood of any reflux of infused agent or medicament would be markedly diminished. The impermeable elastomeric membrane 183 may be placed on or within the mesh braid 181 at any location to include near the inner sheath 175 or near the outer sheath 174 or in the middle between sheaths 174 and 175, but preferably only covering a portion of the braid 181 so that flow is maintained. In this embodiment of the device 171, the expansile anchor 181 comprises an impermeable elastomeric membrane portion 183 and a permeable mesh braid portion 182, thereby providing a level of controllability to the blood flow, to include the blood flow between the device 171 and the vessel wall 200. In a preferred embodiment, the impermeable elastomeric membrane 183 is placed on or within the expansile anchor mesh braid 181 away from the catheter tip 173. This forces the blood to flow through the open portion of the braid 181 as demonstrated by the arrows of FIG. 4B and about and just distal to the distal tip 173 of the anchor catheter device 173. This redirected flow insures enhanced admixing of the injected agent or medicament with the flowing blood.

Further, in the embodiment of the invention of FIGS. 5A-F, a separate flap mechanism 190 is provided that allows forward flow but not reverse flow or reflux. The flap mechanism 190 extends from within the inner sheath 175 in a generally fluted-shape that extends past or distally to the distal tip of the device 173 such that when extended, it has minimal to no effect on the blood flow in the vessel 200, but when rested against the expansile braid 181, restricts or totally prevents blood flow. The separate flap mechanism 190 may be controlled and positioned by movement of the inner sheath 175, by a guide wire, by an additional inner sheath, or other means.

In another embodiment, to further prevent movement or migration of the device 171 during infusion, an attachment mechanism secured to the device 171 shaft at or near the skin insertion site may be provided. This attachment mechanism may vary in configuration from a suture attached to the tissues, to a clip at the skin level, to an anchoring device, or any other means of preventing movement of the catheter.

Figure 6:
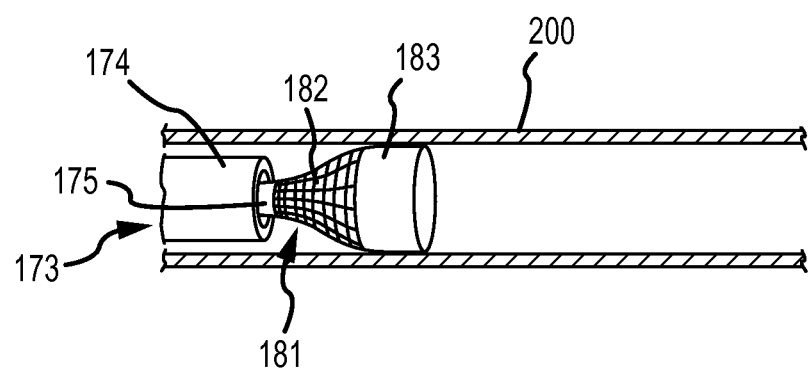
FIG. 6 is a cross-sectional view of the distal tip of the device inserted within the vessel of a patient, the embodiment having an expansile anchor deployed and an inner sheath that is moveable to adjust the degree of cover of the expansile anchor.

In the embodiment of the invention of FIG. 6, the expansile anchor 181 of the anchor catheter device 171 is configured as a mesh braid, as in FIGS. 4A-J and 5A-F, yet is mounted solely to the inner sheath 175 and not additionally mounted to the outer sheath 174. In this embodiment, the expansile anchor 181 is an extension of the distal aspect of the inner sheath 175. When undeployed, the expansile anchor braid 181 is within the lumen of the distal tip 173 of the device 171 and is internal to the outer sheath 174. The expansile anchor braid 181 is extended or deployed by movement of the inner sheath 175 away from or distally to the outer sheath 175 (as depicted in FIG. 6). The expansile anchor braid 181 self-deploys as the inner sheath 175 is moved further away from the outer sheath; the expansile anchor braid 181 deploys so as to rest against the vessel wall 200 and impart a controlled axial force against the vessel wall 200. The expansile anchor braid 181 is configured with a permeable mesh braid portion 182 and an impermeable elastomeric portion 183. To control blood flow and pressure distally, the outer sheath 174 is advanced over the permeable mesh braid portion 182, therein covering at least a portion of the permeable mesh braid portion 182 and thus regulating or throttling blood flow. This embodiment may provide additional flexibility to the anchor catheter device 171.

It should be noted that the features of the embodiments of FIGS. 3, FIGS. 4A-J, FIGS. 5A-F and FIG. 6 may be combined or adapted in any configuration to form embodiments not explicitly depicted or described. For example, the flap mechanism 190 with or without flap mechanism fluted-bell 192, as depicted in FIGS. 5a-f, may be fitted to the embodiment of the device 171 depicted in FIG. 3, or to the embodiment of the device 171 depicted in FIG. 6.

To further prevent movement or migration of the device 171 during infusion, an attachment mechanism secured to the device 171 shaft at or near the skin insertion site may be provided. Such an attachment mechanism may vary in configuration from a suture attached to the tissues, to a clip at the skin level, to an anchoring device, or any other means of preventing movement of the catheter. One configuration of the attachment mechanism near the skin insertion site may take the form of the embodiments of FIGS. 3, FIGS. 4A-J, FIGS. 5A-F, or FIG. 6. The attachment mechanism would be placed coaxially over the outer sheath of any of the embodiments and would be only a few centimeters in total length instead of the elongated catheter configurations previously described. When the tip of the chosen embodiment was in correct position, the slideable attachment mechanism would be moved to a position just within the skin insertion site and expanded within the tract formed by the catheter insertion by moving the outer sheath relative to the inner sheath as previously described. This expanded configuration within the tract or channel formed by the catheter would fix the catheter and prevent movement.

Another similar use may entail placing the attachment mechanism on a long term central venous catheter which may be used for dialysis, plasmaphoresis, and long term drug administration. Usually these central venous catheters are tunneled through a soft tissue tract several centimeters from the puncture site of the vein. Typically they contain a cuff of material on the outer portion of the catheter which resides in the tract and promotes cellular ingrowth into the cuff to help anchor and stabilize the catheter preventing catheter movement and lessening the chance of infection. It takes weeks if not months for substantial cellular ingrowth to occur, and the cuffs placed within the tunneled tracts of the current devices are not particularly effective at anchoring the catheter or preventing infection at this time. One configuration of the current invention would solve these problems. The anchoring mechanism of FIGS. 3, FIGS. 4A-J, FIGS. 5A-F, or FIG. 6 could be placed coaxially over the central venous catheter and either fixed to it in a position that would cause it to reside within the extravascular tunneled tract of the central venous catheter or it may be slideable along the surface of the central venous catheter to a position near the skin exit site of the central venous catheter within the tunneled tract and fixed to the central venous catheter at that point by any one of several means. After the tip of the central venous catheter is positioned, the anchoring mechanism would be positioned within the tunneled tract and expanded as in the foregoing examples against the margins of the tunneled tract to anchor the central venous catheter. The braid in the prior examples may be completely or partially covered with an impermeable substance or with a partially permeable substance, or may contain antibiotics or other substances to inhibit infections or the ingress of bacteria into the tunneled tract. Moreover the anchoring mechanism may be comprised of materials or substances that promote or inhibit cellular ingrowth. Removing the catheters of the current art devices is problematic after cellular ingrowth of the cuffs has occurred as prolonged dissection of the cuffs from the tunneled tract tissues is required. The current invention would provide an anchoring mechanism not requiring cellular ingrowth and an effective barrier to the ingress of bacteria without the need for cellular ingrowth. Hence it would be effective immediately from the time it was inserted and deployed vs. the several weeks to months required by the current devices, and removing the catheter for exchange or complete removal would be greatly simplified.

In fact, the above embodiment may be used on any catheter, tube, needle, probe, or other device within a tract in the human body to anchor or secure it into position within the channel or tract formed by the particular device, including but not limited to nephrostomy, cystostomy, gastrostomy, thoracotomy tubes, drainage catheters, needles or probes for biopsy or treatment, and the like. It may also be utilized to diminish the chance of infection within the tract.

While the detailed descriptions above are principally concerned with a tubular mesh braid as the expansile anchor 181 element that secures the device tip 173 to the wall of the vessel 200 while preserving flow beyond the tip 173, other expansile anchor 181 configurations that accomplish the same action are also feasible, including, but not limited to stent like structures, parallel wires, non parallel wires, spiral elements, circular elements, malecots, tubular elements, laser cut structures, buddy wires, and any structure or component which expands near the distal tip of the catheter and secures it while preserving flow is included by this mention.

The methods of utilizing all of the above configurations are quite similar. In the case of infusion of a substance into the liver and recovering the effluent venous blood, filtering out the toxic agent, and returning it to the body as has been previously described, imaging studies such as CT scans, MRI, or others are utilized to measure the distance between the most cephalad placement of the venous recovery catheter, whether it be the cavoatrial junction or the supradiaphragmatic IVC, and a point just above the renal veins. Measurements are also taken of the dimensions of the IVC. An appropriate sized recovery device is chosen. A catheter is placed in the proper hepatic artery from a femoral puncture for subsequent perfusion of the liver by a concentrated high dose substance. This infusion catheter is usually delivered to the celiac trunk by a guide catheter which may have a special shape for engaging the celiac axis or trunk. It may be the guide catheter described above or a standard guide catheter. In many cases, the anchor infusion catheter described above may be used as the infusion catheter. It is advanced through the guide catheter, through the celiac axis or trunk, and through the common hepatic artery, and the tip placed in the proper hepatic artery. In the case of the anchor catheter, the mesh anchor is deployed stabilizing the catheter tip. The mesh anchor may or may not comprise a partial elastomeric coating which limits flow past the catheter tip as described previously. The recovery device of the current invention, in one configuration or the other, is placed in the IVC and deployed so that the isolation apparatus covers the hepatic venous ostia and creates a hepatic venous effluent collection chamber. Testing is done to determine if the placement is appropriate by injection of contrast in a retrograde manner through the recovery catheter and into the hepatic venous effluent collection chamber, and demonstrating that there is no leakage from the isolated segment. Contrast is injected into the distal IVC to determine that there is good return through flow to the right atrium. Hepatic venous effluent will be collected, and the hepatic arterial infusion will begin through the hepatic artery infusion catheter. The venous effluent will be collected and pumped and filtered and returned as in the prior art devices for a period of time. After the arterial infusion is complete, the infusion catheter will be removed. In the case of the anchor catheter, the distal braid is collapsed by advancing the inner member with respect to the outer member. The venous effluent collection and treatment will continue for a prescribed period to prevent any delayed washout of the concentrated high dose substance from the liver into the systemic circulation. After a period of time, the chosen recovery device will then be collapsed, retracted, and removed from the body.

As to the method of utilizing a guide catheter with or as an integrated component of the current invention device 171, usually the guide catheter is placed coaxially over a diagnostic catheter. The diagnostic catheter is then utilized to catheterize the origin of the selected vessel, whether it be a coronary artery, a carotid artery, the celiac artery, or any other selected artery. The guide catheter 171 of the current invention is then advanced over the tip of the diagnostic catheter to a point in the proximal selected artery. The anchor 181 of the current invention device 171 may then be deployed and the diagnostic catheter removed. The interventional catheter, whether it be a stent delivery catheter, an angioplasty catheter, atherectomy device, infusion catheter, or other type of catheter, will be advanced coaxially through the guide catheter of the current invention. In the case of tortuous anatomy in the selected artery, the anchored guide catheter of the current invention supports the advancement of the interventional catheter even down tortuous side branches and the like. This is of importance in accessing a point for infusion of a substance or for accessing a lesion distally placed in the selected artery. In the case of a stenotic lesion, the anchored guide catheter of the current invention supports the advancement of a guide wire through a narrow stenotic lesion, or even through a complete occlusion, and allows subsequent passage of the interventional catheter through a narrowed stenotic lesion. Forward pressure on the catheter will not cause it to dislodge the guide catheter of the current invention as that guide catheter is anchored securely within the orifice of the vessel. The problems with the prior art guide catheters are hence obviated, the lesions treated with less effort, less time, less cost, and less risk to the patient.

To provide further clarity to the Detailed Description provided herein in the associated drawings, the following list of components and associated numbering are provided as follows:

| Reference No. | Component |
| --- | --- |
| 100 | patient |
| 141 | aorta |
| 142 | heart |
| 143 | left anterior descending coronary artery |
| 144 | right coronary artery |
| 145 | left subclavian arteries |
| 146 | right subclavian arteries |
| 147 | right common carotid artery |
| 148 | left common carotid artery |
| 149 | catheter positioning point |
| 150 | stent placement point |
| 152 | stenosis point |
| 154 | superior mesenteric artery |
| 155 | left renal artery |
| 156 | right renal artery |
| 158 | guide catheter positioning point |
| 159 | left main coronary artery |
| 160 | celiac artery |
| 161 | celiac trunk |
| 162 | splenic artery |
| 163 | left gastric artery |
| 164 | common hepatic artery |
| 165 | proper hepatic artery |
| 166 | gastroduodenal arteries |
| 167 | right gastric artery |
| 168 | left hepatic artery |
| 169 | right hepatic artery |
| 170 | artery point |
| 171 | anchor catheter device |
| 172 | anchor catheter proximal tip |
| 173 | anchor catheter distal tip |
| 174 | outer sheath |
| 175 | inner sheath |
| 176 | locking mechanism |
| 178 | hub |
| 179 | distal end of hub |
| 181 | expansile anchor |
| 182 | permeable mesh braid |
| 183 | impermeable elastomeric membrane |
| 190 | flap mechanism |
| 192 | flap mechanism fluted-bell |
| 200 | vessel wall |

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter apparatus comprising:
a catheter body having a proximal portion, a distal portion with a distal tip, and an inner sheath substantially fitting within an outer sheath, said distal portion further having an expansile anchor mechanism directly connected with the inner sheath and outer sheath, said anchor mechanism deployable by axial movement of said inner sheath within said outer sheath when said catheter apparatus is inserted within a blood vessel, said anchor mechanism comprising a tubular mesh braid having permeable and impermeable portions arranged axially in series so as to allow the level of blood flow or reflux within the blood vessel to be regulated or throttled by advancing the outer sheath relative to the inner sheath, wherein the impermeable portion comprises an impermeable membrane placed on or within the impermeable portion while leaving the permeable portion uncovered and open to blood flow therethrough, and
wherein the impermeable portion of the deployed anchor mechanism allows antegrade blood flow beyond the distal tip while limiting the blood flow to cause pressure in the blood vessel distal to the distal tip to be less than pressure in the blood vessel proximal to the distal tip.

2. The apparatus of claim 1, wherein the impermeable portion of the tubular mesh braid substantially includes a portion of the expansile anchor mechanism that engages the blood vessel.

3. The apparatus of claim 2, wherein the apparatus further comprises a flap mechanism associated with one or more of said inner sheath and said anchor mechanism, wherein said flap mechanism allows forward blood flow and prevents reverse blood flow.

4. The apparatus of claim 3, wherein the flap mechanism is configured to be positioned over at least a portion of the impermeable portion of the tubular mesh braid to allow for forward blood flow and prevent reverse blood flow.

5. The apparatus of claim 3, wherein the flap mechanism is translatable with respect to the inner sheath.

6. The apparatus of claim 3, wherein said flap mechanism has a distal end having one or more of a fluted or conical shape.

7. The apparatus of claim 3, wherein at least a portion of said flap mechanism is disposed within the inner sheath.

8. The apparatus of claim 3, wherein said flap mechanism has minimal effect on the blood flow when a distal end of said flap mechanism is extended past the distal portion of the catheter body.

9. The apparatus of claim 3, wherein said flap mechanism conforms to a distal surface of the deployed anchor mechanism when the distal end of the flap mechanism is retracted and rested against the distal surface, thereby restricting blood flow in the blood vessel.

10. The apparatus of claim 1, further comprising a guide wire associated with said catheter body.

11. The apparatus of claim 1, wherein said distal portion when deployed is configured for direct delivery of at least one of a medicament and medical device once the expansile anchor mechanism is deployed.

12. The apparatus of claim 1, wherein the anchor mechanism has a first end and a second end opposite the first end, the first end being directly connected to a distal end of the inner sheath and the second end being directly connected to a distal end of the outer sheath.

13. The apparatus of claim 1, wherein one or more of the permeable or impermeable portions extend around at least a full circumference of the tubular mesh braid.

14. The apparatus of claim 1, wherein advancing the outer sheath relative to the inner sheath causes the anchor mechanism to regulate or throttle blood flow in a portion of the blood vessel distal to the distal portion of the catheter body.

15. The apparatus of claim 1, wherein causing the anchor mechanism to regulate or throttle blood flow lowers pressure in a portion of the blood vessel distal to the distal portion of the catheter body.

16. The apparatus of claim 1, wherein a proportion of the permeable and impermeable portions exposed to blood flow is varied by advancing the outer sheath relative to the inner sheath.

17. The apparatus of claim 1, wherein the permeable and impermeable portions allow the level of blood flow through the tubular mesh braid to be regulated or throttled by advancing the outer sheath relative to the inner sheath.

18. A catheter apparatus comprising:
a catheter body having a proximal portion, a distal portion with a distal tip, and an inner sheath substantially fitting within an outer sheath, said distal portion further having an expansile anchor mechanism comprising a tubular mesh material, said anchor mechanism directly connected with the inner sheath and the outer sheath, said anchor mechanism having a first unexpanded configuration and a second expanded configuration, said first unexpanded configuration permitting axial movement of said catheter in a blood vessel, and said second expanded configuration bringing said distal portion into anchoring contact with said blood vessel, said anchor mechanism comprising a tubular mesh braid having permeable and impermeable portions arranged axially in series so as to allow the level of blood flow or reflux within the blood vessel to be regulated or throttled by advancing the outer sheath relative to the inner sheath, wherein the impermeable portion comprises an impermeable membrane placed on or within the impermeable portion while leaving the permeable portion uncovered and open to blood flow therethrough, and
wherein the impermeable portion of the deployed anchor mechanism allows antegrade blood flow beyond the distal tip while limiting the blood flow to cause pressure in the blood vessel distal to the distal tip to be less than pressure in the blood vessel proximal to the distal tip.

19. The apparatus according to claim 18, wherein said second expanded configuration substantially limits the flow of blood around said distal portion when said second expanded configuration is employed.

20. The apparatus according to claim 18, wherein said second expanded configuration is achieved by axial movement of said inner sheath within said outer sheath.

21. The apparatus according to claim 18, wherein said second expanded configuration comprises an outer non-mesh material contacting said blood vessel, said non-mesh material being adjacent to said mesh material.

22. The apparatus according to claim 18, wherein the anchor mechanism has a first end and a second end opposite the first end, the first end being directly connected to a distal end of the inner sheath and the second end being directly connected to a distal end of the outer sheath.

23. The apparatus according to claim 18, wherein the impermeable portion of the tubular mesh braid substantially includes a portion of the expansile anchor mechanism that engages the body channel.

24. The apparatus according to claim 23, wherein the apparatus further comprises a flap mechanism associated with one or more said inner sheath or said anchor mechanism, wherein said flap mechanism allows forward blood flow and prevents reverse blood flow.

25. The apparatus according to claim 24, wherein the flap mechanism is configured to be positioned over at least a portion of the impermeable portion of the tubular mesh braid to allow for forward blood flow and prevent reverse blood flow.

26. The apparatus according to claim 24, wherein the flap mechanism is translatable with respect to the inner sheath.

27. The apparatus of claim 24, wherein said flap mechanism has a distal end having one or more of a fluted or conical shape.

28. The apparatus of claim 24, wherein at least a portion of said flap mechanism is disposed within the inner sheath.

29. The apparatus of claim 24, wherein said flap mechanism has minimal effect on the blood flow when a distal end of said flap mechanism is extended past the distal portion of the catheter body.

30. The apparatus of claim 24, wherein said flap mechanism conforms to a distal surface of the deployed anchor mechanism when the distal end of the flap mechanism is retracted and rested against the distal surface, thereby restricting blood flow in the blood vessel.

31. The apparatus of claim 18, wherein one or more of the permeable or impermeable portions extend around the circumference of the tubular mesh braid.

32. The apparatus of claim 18, wherein advancing the outer sheath relative to the inner sheath causes the anchor mechanism to regulate or throttle blood flow in a portion of the blood vessel distal to the distal tip of the catheter body.

33. The apparatus of claim 18, wherein causing the anchor mechanism to regulate or throttle blood flow lowers pressure in a portion of the blood vessel distal to the distal portion of the catheter body.

34. The apparatus of claim 18, wherein a proportion of the permeable and impermeable portions exposed to blood flow is varied by advancing the outer sheath relative to the inner sheath.

35. The apparatus of claim 18, wherein the permeable and impermeable portions allow the level of blood flow through the tubular mesh braid to be regulated or throttled by advancing the outer sheath relative to the inner sheath.

36. A catheter apparatus comprising:
a catheter body having a proximal portion, a distal portion, and an inner sheath substantially fitting within an outer sheath, said distal portion further having an expansile anchor mechanism directly connected with one or more of the inner sheath or outer sheath, said anchor mechanism deployable by axial movement of said inner sheath or outer sheath relative to one another when said catheter apparatus is inserted within a body channel, said anchor mechanism comprising a tubular mesh braid having permeable and impermeable portions arranged axially in series so as to allow the level of fluid flow or reflux within the body channel to be regulated or throttled by axial movement of said inner sheath or said outer sheath relative to one another, wherein the impermeable portion comprises an impermeable membrane placed on or within the impermeable portion while leaving the permeable portion uncovered and open to blood flow therethrough, and
wherein the impermeable portion of the deployed anchor mechanism allows antegrade fluid flow beyond the distal tip while limiting the fluid flow to cause pressure in the body channel distal to the distal tip to be less than pressure in the body channel proximal to the distal tip.

37. The catheter apparatus of claim 36, wherein the body channel comprises a blood vessel and the fluid flow within the body channel comprises blood flow.

38. The catheter apparatus of claim 36, wherein the impermeable portion of the tubular mesh braid substantially includes a portion of the expansile anchor mechanism that engages the body channel.

39. The catheter apparatus of claim 38, wherein the apparatus further comprises a flap mechanism associated with one or more of said inner sheath and said anchor mechanism, wherein said flap mechanism allows forward blood flow and prevents reverse blood flow.

40. The catheter apparatus of claim 39, wherein said flap mechanism has a distal end having one or more of a fluted or conical shape.

41. The catheter apparatus of claim 39 wherein at least a portion of said flap mechanism is disposed within the inner sheath.

42. The catheter apparatus of claim 39, wherein said flap mechanism has minimal effect on the blood flow when a distal end of said flap mechanism is extended past the distal portion of the catheter body.

43. The catheter apparatus of claim 39, wherein said flap mechanism conforms to a distal surface of the deployed anchor mechanism when the distal end of the flap mechanism is retracted and rested against the distal surface, thereby restricting blood flow in the blood vessel.

44. The catheter apparatus of claim 39, wherein the flap mechanism is configured to be positioned over at least a portion of the impermeable portion of the tubular mesh braid to allow for forward blood flow and prevent reverse blood flow.

45. The catheter apparatus of claim 39, wherein the flap mechanism is translatable with respect to the inner sheath.

46. The catheter apparatus of claim 36, further comprising a guide wire associated with said catheter body.

47. The catheter apparatus of claim 36, wherein said distal portion when deployed is configured for direct delivery of at least one of a medicament and medical device once the expansile anchor mechanism is deployed.

48. The catheter apparatus of claim 36, wherein one or more of the permeable or impermeable portions extend around at least a full circumference of the tubular mesh braid.

49. The catheter apparatus of claim 36, wherein advancing the outer sheath relative to the inner sheath causes the anchor mechanism to regulate or throttle blood flow in a portion of the blood vessel distal to the distal portion of the catheter body.

50. The catheter apparatus of claim 36, wherein causing the anchor mechanism to regulate or throttle blood flow lowers pressure in a portion of the blood vessel distal to the distal portion of the catheter body.

51. The catheter apparatus of claim 36, wherein a proportion of the permeable and impermeable portions exposed to blood flow is varied by advancing the outer sheath relative to the inner sheath.

52. The catheter apparatus of claim 36, wherein the permeable and impermeable portions allow the level of blood flow through the tubular mesh braid to be regulated or throttled by advancing the outer sheath relative to the inner sheath.

* * * * *